United States Patent
Tsubaki et al.

(10) Patent No.: US 7,442,753 B2
(45) Date of Patent: Oct. 28, 2008

(54) POLYMER COMPOUND AND BLOCK POLYMER COMPOUND

(75) Inventors: Keiichiro Tsubaki, Kawasaki (JP); Koichi Sato, Atsugi (JP); Ikuo Nakazawa, Zama (JP); Ryuji Higashi, Atsugi (JP); Sakae Suda, Sagamihara (JP); Masayuki Ikegami, Atsugi (JP); Keiko Yamagishi, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 409 days.

(21) Appl. No.: 10/546,536

(22) PCT Filed: Oct. 27, 2004

(86) PCT No.: PCT/JP2004/016289

§ 371 (c)(1),
(2), (4) Date: Aug. 22, 2005

(87) PCT Pub. No.: WO2005/042594

PCT Pub. Date: May 12, 2005

(65) Prior Publication Data

US 2006/0144287 A1    Jul. 6, 2006

(30) Foreign Application Priority Data

Oct. 31, 2003 (JP) .............................. 2003-372462
Dec. 26, 2003 (JP) .............................. 2003-434553
May 7, 2004 (JP) .............................. 2004-139053

(51) Int. Cl.
*C08F 22/14* (2006.01)
*C08F 212/00* (2006.01)
*C08F 216/12* (2006.01)

(52) U.S. Cl. ............. 526/323; 526/317.1; 526/334; 526/333; 526/319; 526/320; 524/505; 524/556; 524/612

(58) Field of Classification Search ............. 524/556, 524/505, 612; 526/317.1, 319, 333, 271, 526/279, 323, 334, 320; 560/183

See application file for complete search history.

(56) References Cited

U.S. PATENT DOCUMENTS

| | | | | |
|---|---|---|---|---|
| 4,313,124 | A | 1/1982 | Hara | 346/140 R |
| 4,345,262 | A | 8/1982 | Shirato et al. | 346/140 R |
| 4,459,600 | A | 7/1984 | Sato et al. | 346/140 R |
| 4,463,359 | A | 7/1984 | Ayata et al. | 346/1.1 |
| 4,558,333 | A | 12/1985 | Sugitani et al. | 346/140 R |
| 4,723,129 | A | 2/1988 | Endo et al. | 346/1.1 |
| 4,740,796 | A | 4/1988 | Endo et al. | 346/1.1 |
| 5,085,698 | A | 2/1992 | Ma et al. | 106/20 |
| 7,004,579 | B2 | 2/2006 | Sato et al. | 347/105 |
| 7,056,972 | B2 | 6/2006 | Nakazawa et al. | 524/505 |
| 7,067,590 | B2 | 6/2006 | Sato et al. | 525/299 |
| 2005/0033010 | A1 | 2/2005 | Sato et al. | 528/80 |
| 2005/0131102 | A1 | 6/2005 | Nakazawa et al. | 523/160 |
| 2005/0140762 | A1 | 6/2005 | Sato et al. | 347/100 |
| 2005/0197424 | A1 | 9/2005 | Higashi et al. | 523/160 |
| 2005/0209367 | A1 | 9/2005 | Sato et al. | 523/161 |
| 2005/0219277 | A1 | 10/2005 | Sato et al. | 347/1 |
| 2005/0239918 | A1 | 10/2005 | Nakazawa et al. | 523/160 |
| 2005/0249925 | A1 | 11/2005 | Ikegami et al. | 428/195.1 |
| 2006/0004124 | A1 | 1/2006 | Tsubaki et al. | 523/160 |
| 2006/0047015 | A1 | 3/2006 | Duda et al. | 523/160 |
| 2006/0050117 | A1 | 3/2006 | Sato et al. | 347/100 |
| 2006/0057485 | A1 | 3/2006 | Teshima et al. | 430/108.8 |
| 2006/0100310 | A1 | 5/2006 | Nakazawa et al. | 523/160 |
| 2006/0128828 | A1 | 6/2006 | Sato et al. | 523/160 |
| 2006/0146087 | A1 | 7/2006 | Sato et al. | 347/21 |
| 2006/0160975 | A1 | 7/2006 | Suda et al. | 526/330 |
| 2006/0178468 | A1 | 8/2006 | Sato et al. | 524/556 |
| 2006/0221117 | A1 | 10/2006 | Sato et al. | 347/21 |

FOREIGN PATENT DOCUMENTS

| | | | |
|---|---|---|---|
| EP | 1 357 138 A1 | | 10/2003 |
| EP | 1357138 A1 | * | 10/2003 |
| JP | S59-123670 | | 7/1984 |
| JP | S59-138461 | | 8/1984 |
| JP | H11-322942 | | 11/1999 |

OTHER PUBLICATIONS

Saifur Rahman et al., *Cationic Polymerization of Vinyl Ether with a Benzoate Pendant: The Formation of Long-Lived Polymers and the Identification of Side Reactions*, Journal of Polymer Science—Part A—Polymer Chemistry, Wiley & Sons, New York, NY, U.S.A., vol. 38, No. 24, Dec. 2000, pp. 4362-4372.

* cited by examiner

*Primary Examiner*—Randy Gulakowski
*Assistant Examiner*—Michael M Bernshteyn
(74) *Attorney, Agent, or Firm*—Fitzpatrick, Cella, Harper & Scinto

(57) ABSTRACT

A compound represented by the following general formula (1): (1) wherein A represents an alkenyl ether group which may be substituted; B represents a linear or branched alkylene group having 1 to 15 carbon atoms which may be substituted; m represents an integer from 0 to 30; when m is larger than 1, B may be different from each other; D represents a single bond or a linear or branched alkylene group having 1 to 10 carbon atoms which may be substituted; E represents any one of an aromatic ring which may be substituted, a condensed ring which may be substituted, and a structure formed by bonding through single bonds at most three aromatic rings which may be substituted; R represents a hydrogen atom, a linear or branched alkyl group having 1 to 5 carbon atoms which may be substituted, or an aromatic ring which may be substituted; n represents a positive number larger than 1; a COOR group in the formula is substituted into the aromatic ring of E; and a hydrogen atom in the aromatic ring, which is not substituted with COOR, may be substituted.

2 Claims, 1 Drawing Sheet

POLYMER COMPOUND AND BLOCK POLYMER COMPOUND

TECHNICAL FIELD

The present invention relates to a novel block polymer compound useful for various functional materials, a polymer-containing composition, a recording material such as an ink or a toner, an image forming method, and an image forming apparatus.

BACKGROUND ART

An ink composition or a toner composition has been prepared conventionally by dissolving or dispersing a colorant. Various polymer materials have been used preferably therefore, and examples of the polymer materials include a styryl, acryl, or methacrylic polymer compound. A colorant composition containing a solvent or water as a base material generally employs a polymer material preferably having an ionic functional group, as an attempt at improving dispersibility of the colorant such as a pigment.

Meanwhile, a polymer compound having a polyvinyl ether main chain is also known as a polymer material having a flexible polymer chain. However, an ionic functional group is rarely introduced into a repeating unit of the polymer compound. Candidates for the ionic functional group such as carboxylic acids and carboxylate esters are reported, but more stable compounds are actually demanded (see Journal of Polymer Science, Part A, Polymer Chemistry, 27, 3303-3314 (1989)).

An aqueous dispersing material contains a functional substance, and conventionally known examples of the functional material include: pesticides such as a herbicide and an insecticide; pharmaceuticals such as an anticancer agent, an anti-allergic drug, and an anti-inflammatory; and colorants each containing a colorant such as an ink and a toner. A digital printing technique has recently progressed at a remarkable rate. Typical examples of the digital printing technique include an electrophotographic technique and an ink jet technique, and the digital printing technique has increasingly enhanced its raison d'etre recently as an image forming technique in an office, home, or the like.

Of those, the ink jet technique has such a remarkable feature that it provides a compact, low-power consumption direct recording method. Further, miniaturization of nozzles or the like has rapidly enhanced image quality. An example of the ink jet technique involves: evaporating and bubbling an ink supplied from an ink tank by heating with a heater in a nozzle; and ejecting the ink, to thereby form an image on a recording medium. Another example thereof involves ejecting an ink from a nozzle by vibrating a piezoelectric element.

The ink used in such methods usually employs an aqueous dye solution, and may result in bleeding when overlapping colors or a phenomenon called feathering in a grain direction of paper at recording positions on the recording medium. Use of a pigment-dispersed ink has been studied for solving such problems (see U.S. Pat. No. 5,085,698). However, much improvement is still desired.

DISCLOSURE OF THE INVENTION

The present invention has been made in view of the above, and an object of the present invention is to provide a polymer compound suitable for improving dispersibility of a colorant or a solid substance in an ink composition or a toner composition.

Further, the present invention provides a novel compound which is necessary for and stable in production of the polymer compound.

Furthermore, the present invention provides an image forming method and an image forming apparatus employing a recording material such as an ink composition or a toner composition which uses the polymer compound.

The inventors of the present invention have made intensive studies on the prior art and the problems, and have completed the present invention described below.

The present invention relates to a compound represented by the following general formula (1).

$$A\text{-}(BO)_m\text{-}D\text{-}E\text{-}(COOR)_n \qquad (1)$$

(In the formula: A represents an alkenyl ether group which may be substituted; B represents a linear or branched alkylene group having 1 to 15 carbon atoms which may be substituted; m represents an integer from 0 to 30; when m is larger than 1, B may be different from each other; D represents a single bond or a linear or branched alkylene group having 1 to 10 carbon atoms which may be substituted; E represents any one of an aromatic ring which may be substituted, a condensed ring which may be substituted, and a structure formed by bonding through single bonds at most three aromatic rings which may be substituted; R represents a hydrogen atom, a linear or branched alkyl group having 1 to 5 carbon atoms which may be substituted, or an aromatic ring which may be substituted; n represents a positive number larger than 1; a COOR group in the formula is substituted into the aromatic ring of E; and a hydrogen atom in the aromatic ring, which is not substituted with COOR, may be substituted.)

Further, the present invention relates to a polymer compound having a repeating unit structure represented by the following general formula (2).

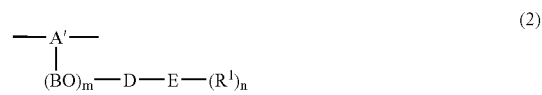

(2)

(In the formula: A' represents a polyalkenyl ether group which may be substituted; B represents a linear or branched alkylene group having 1 to 15 carbon atoms which may be substituted; m represents an integer from 0 to 30; when m is larger than 1, B may be different from each other; D represents a single bond or a linear or branched alkylene group having 1 to 10 carbon atoms which may be substituted; E represents any one of an aromatic ring which may be substituted, a condensed ring which may be substituted, and a structure formed by bonding through single bonds at most three aromatic rings which may be substituted; $R^1$ represents —COOH, —COOR$^4$, or —COO$^-$M; $R^4$ represents a linear or branched alkyl group having 1 to 5 carbon atoms which may be substituted or an aromatic ring which may be substituted; M represents a monovalent or polyvalent metal cation; n represents a number larger than 1; an $R^1$ group in the formula is substituted into the aromatic ring of E; and a hydrogen atom in the aromatic ring, which is not substituted with $R^1$, may be substituted.)

Further, the present invention relates to a composition including the polymer compound of the present invention, a functional substance, and a solvent or dispersing medium.

Further, the present invention relates to a recording material in which the functional substance is a colorant.

Further, the present invention relates to an image forming method including the step of recording an image on a recording medium by applying the recording material of the present invention on the recording medium.

Further, the present invention relate to an image forming apparatus including: image recording means for recording an image on a recording medium by applying the recording material on the recording medium; and drive means for driving the image recording means.

BEST MODE FOR CARRYING OUT THE INVENTION

Figure 1:
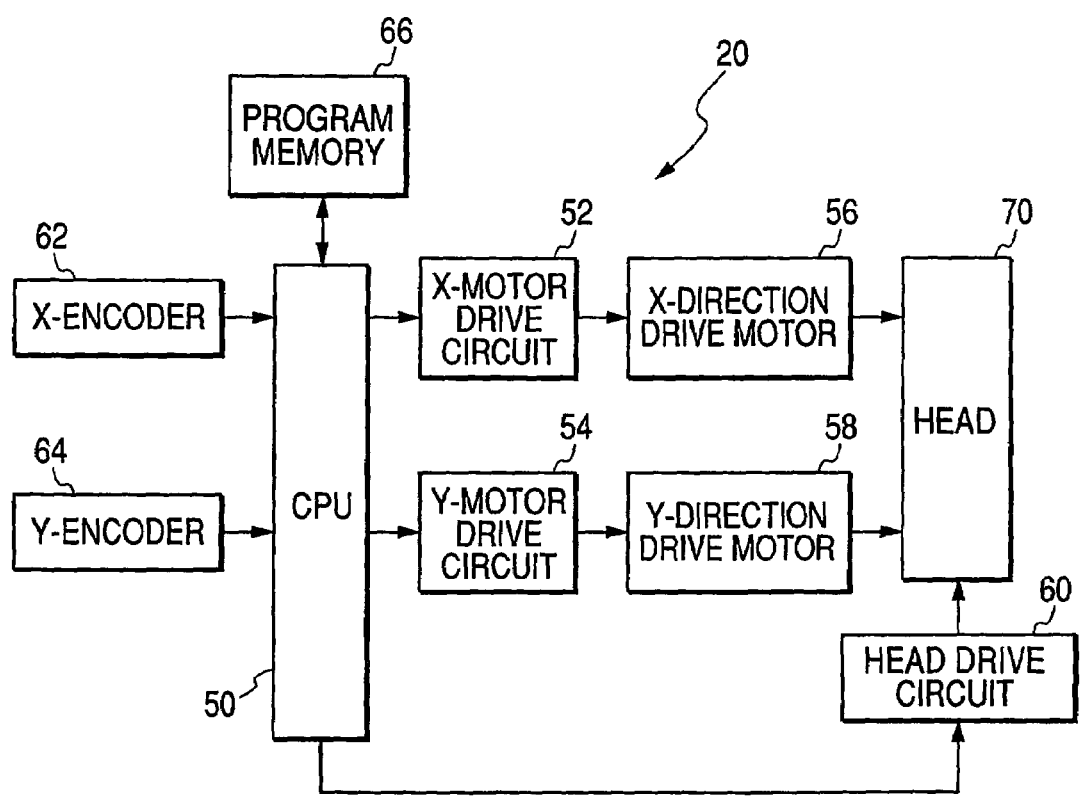
FIG. 1 is a block diagram showing a structure of an ink jet recording apparatus.

Hereinafter, the present invention will be described in detail.

That is, the present invention relates to a compound represented by the following general formula (1).

In the general formula (1), A represents an alkenyl ether group which may be substituted. The alkenyl ether group has an ether group bonded to a vinyl group, and the vinyl group may be substituted with a linear or branched alkylene group having 1 to 5 carbon atoms or with a halogen atom.

B represents a linear or branched alkylene group having 1 to 15 carbon atoms which may be substituted. Examples of a substituent to the alkylene group include ethylene, propylene, and butylene. m represents an integer from 0 to 30, preferably from 1 to 10. When m is larger than 1, B may be different from each other. D represents a single bond or a linear or branched alkylene group having 1 to 10 carbon atoms which may be substituted. Examples of the alkylene group include methylene, ethylene, propylene, butylene, pentylene, hexylene, heptylene, and octylene. E represents any one of an aromatic ring which may be substituted, a condensed ring which may be substituted, and a structure formed by bonding through single bonds at most three aromatic rings which may be substituted. Examples of an aromatic ring structure include phenyl, pyridylene, pyrimidyl, naphthyl, anthranyl, phenanthrenyl, thiophenyl, and furanyl. R represents a hydrogen atom, a linear or branched alkyl group having 1 to 5 carbon atoms which may be substituted, or an aromatic ring which may be substituted. Examples of the aromatic ring structure include a phenyl group, a pyridyl group, and a biphenyl group. Examples of the substituent include an alkyl group and an alkoxy group. n represents a positive number larger than 1. A COOR group in the formula is substituted into the aromatic ring of E. A hydrogen atom in the aromatic ring, which is not substituted with COOR, may be substituted. Examples of the substituent include an alkyl group, an alkoxy group, and a halogen atom.

An example of a preferable structure of the compound represented by the general formula (1) includes a compound represented by the following general formula (4).

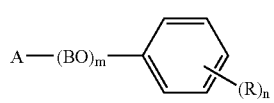

(In the formula: A represents an alkenyl ether group which may be substituted; B represents a linear or branched alkylene group having 1 to 15 carbon atoms which may be substituted; m represents an integer from 0 to 30; when m is larger than 1, B may be different from each other; R represents a hydrogen atom, a linear or branched alkyl group having 1 to 5 carbon atoms which may be substituted, or an aromatic ring which may be substituted; n represents a positive number larger than 1; a COOR group in the formula is substituted into the aromatic ring of E; and a hydrogen atom in the aromatic ring, which is not substituted with COOR, may be substituted.)

An example of a more preferable structure of the compound represented by the general formula (1) includes a compound represented by the following general formula (5).

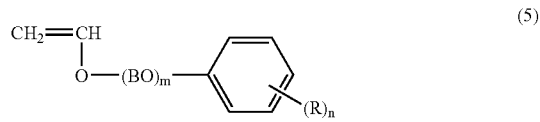

(In the formula: B represents a linear or branched alkylene group having 1 to 15 carbon atoms which may be substituted; m represents an integer from 0 to 30; when m is larger than 1, B may be different from each other; R represents a hydrogen atom, a linear or branched alkyl group having 1 to 5 carbon atoms which may be substituted, or an aromatic ring which may be substituted; n represents a positive number larger than 1; a COOR group in the formula is substituted into the aromatic ring of E; and a hydrogen atom in the aromatic ring, which is not substituted with COOR, may be substituted.)

Further, specific examples of the compound represented by the general formula (1) include the compounds listed below.

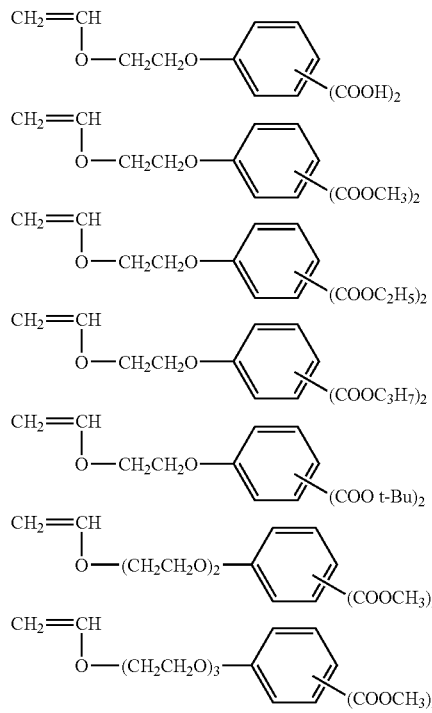

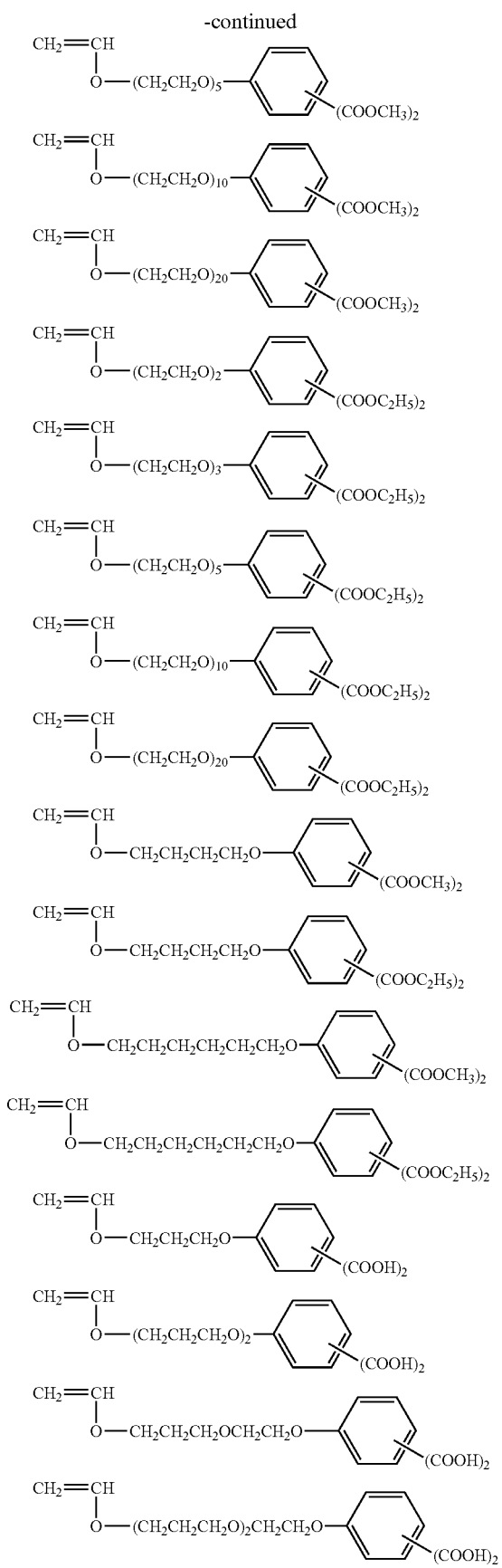
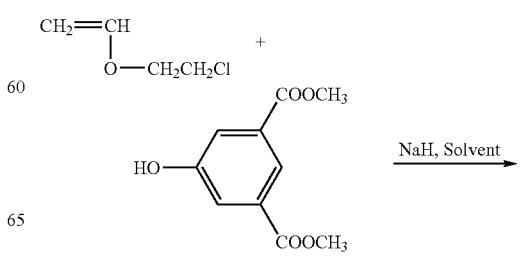
Further, protons at position 3 and position 5 of a benzene ring in each of the above compounds are preferably substituted with a carboxylic acid or a carboxylate ester.
A typical example of a synthesis method for the compound represented by the general formula (1) includes a method involving esterification represented by the following reaction formula.

-continued

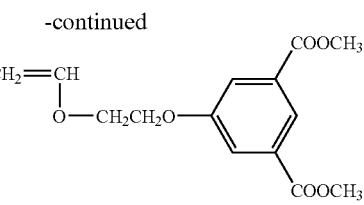

Further, the present invention relates to a polymer compound having a repeating unit structure represented by the following general formula (2).

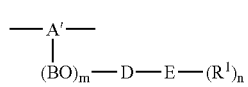

(In the formula: A' represents a polyalkenyl ether group which may be substituted; B represents a linear or branched alkylene group having 1 to 15 carbon atoms which may be substituted; m represents an integer from 0 to 30; when m is larger than 1, B may be different from each other; D represents a single bond or a linear or branched alkylene group having 1 to 10 carbon atoms which may be substituted; E represents any one of an aromatic ring which may be substituted, a condensed ring which may be substituted, and a structure formed by bonding through single bonds at most three aromatic rings which may be substituted; $R^1$ represents —COOH, —COOR$^4$, or —COO$^-$M; $R^4$ is a linear or branched alkyl group having 1 to 5 carbon atoms which may be substituted or an aromatic ring which may be substituted; M represents a monovalent or polyvalent metal cation; n represents a positive number larger than 1; an $R^1$ group in the formula is substituted into the aromatic ring of E; and a hydrogen atom in the aromatic ring, which is not substituted with $R^1$, may be substituted.)

In the general formula (2), A' represents a polyalkenyl ether group which may be substituted. The polyalkenyl ether group has a polymerized vinyl ether group. The vinyl ether group may be substituted with a linear or branched alkylene group having 1 to 5 carbon atoms or with a halogen atom.

B represents a linear or branched alkylene group having 1 to 15 carbon atoms which may be substituted. Examples of a substituent to the alkylene group include ethylene, propylene, and butylene.

m represents an integer from 0 to 30, preferably from 1 to 10. When m is larger than 1, B may be different from each other.

D represents a single bond or a linear or branched alkylene group having 1 to 10 carbon atoms which may be substituted. Examples of the alkylene group include methylene, ethylene, propylene, butylene, pentylene, hexylene, heptylene, and octylene.

E represents any one of an aromatic ring which may be substituted, a condensed ring which may be substituted, and a structure formed by bonding through single bonds at most three aromatic rings which may be substituted. Examples of an aromatic ring structure include phenyl, pyridylene, pyrimidyl, naphthyl, anthranyl, phenanthrenyl, thiophenyl, and furanyl.

$R^1$ represents any one of —COOH, —COOR$^4$, and —COO$^-$M. $R^4$ represents a linear or branched alkyl group having 1 to 5 carbon atoms which may be substituted or an aromatic ring which may be substituted. Examples of the aromatic ring structure include a phenyl group, a pyridyl group, and a biphenyl group. Examples of the substituent include an alkyl group and an alkoxy group. M represents a monovalent or polyvalent metal cation. Specific examples of M include: monovalent metal cations such as sodium, potassium, and lithium; and polyvalent metal cations such as magnesium, calcium, nickel, and iron. When M represents a polyvalent metal cation, M forms a counter ion with two or more COO$^-$ anions.

n represents a positive number larger than 1. An $R^1$ group in the formula is substituted into the aromatic ring of E. In addition, a hydrogen atom in the aromatic ring, which is not substituted with $R^1$, may be substituted. Examples of the substituent include an alkyl group, an alkoxy group, and a halogen atom.

An example of a preferable structure of the repeating unit structure represented by the general formula (2) includes a compound represented by the following general formula (6).

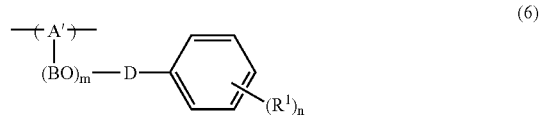

(In the formula: A' represents an alkenyl ether group which may be substituted; B represents a linear or branched alkylene group having 1 to 15 carbon atoms which may be substituted; m represents an integer from 0 to 30; when m is larger than 1, B may be different from each other; D represents a single bond or linear or branched alkylene group having 1 to 10 carbon atoms which may be substituted; $R^1$ represents —COOH, —COOR$^4$, or —COO$^-$M; $R^4$ is a linear or branched alkylene group having 1 to 5 carbon atoms which may be substituted or an aromatic ring which may be substituted; M represents a monovalent or polyvalent metal cation; n represents a positive number larger than 1; and a hydrogen atom in the aromatic ring in the formula, which is not substituted with $R^1$, may be substituted.)

Further, an example of a more preferable structure of the repeating unit structure represented by the general formula (2) includes a structure represented by the following general formula (7).

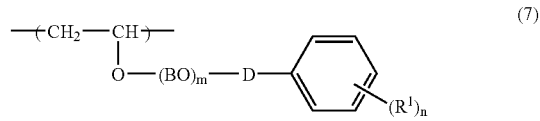

(In the formula: B represents a linear or branched alkylene group having 1 to 15 carbon atoms which may be substituted; m represents an integer from 0 to 30; when m is larger than 1, B may be different from each other; D represents a single bond or a linear or branched alkylene group having 1 to 10 carbon atoms which may be substituted; $R^1$ represents any one of the structures represented by —COOH, —COOR$^4$, and —COO$^-$M; $R^4$ is a linear or branched alkylene group having 1 to 5 carbon atoms which may be substituted or an aromatic ring which may be substituted; M represents a monovalent or polyvalent metal cation; n represents a positive number larger than 1; and a hydrogen atom in the aromatic ring, which is not substituted with $R^1$, may be substituted.)

Specific examples of the repeating unit structure represented by the general formula (2) include the following structures.

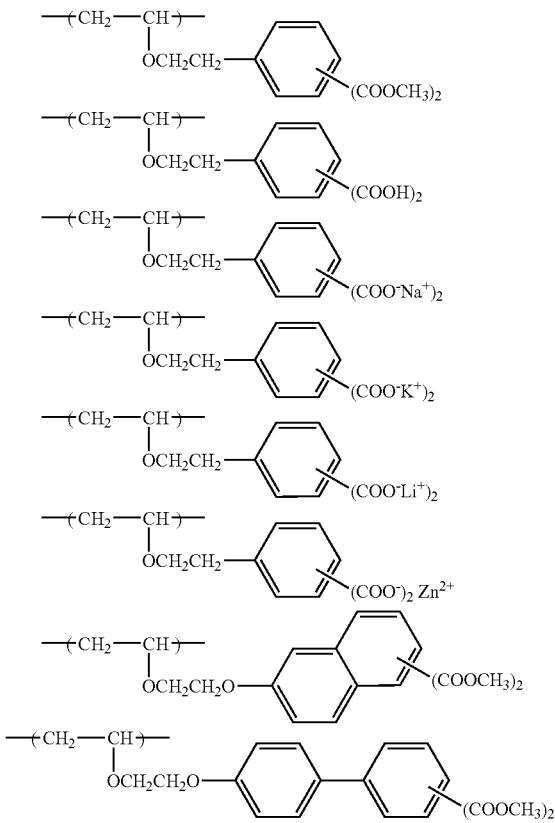

Preferable specific examples thereof include the following.

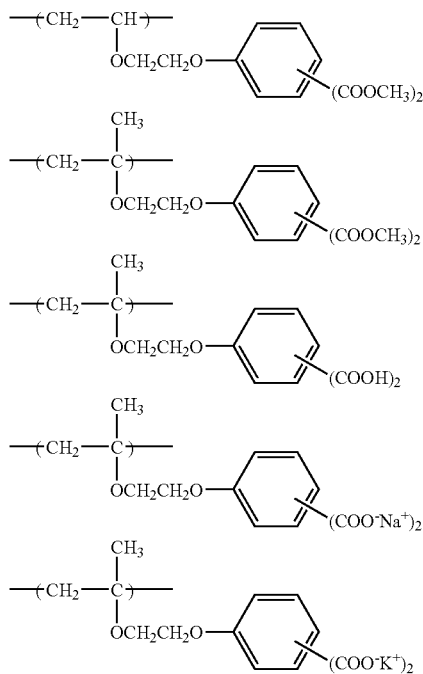

-continued

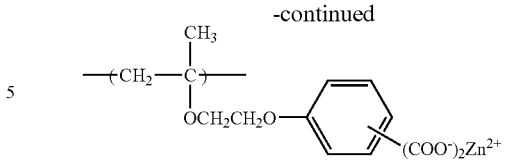

Further, protons at position 3 and position 5 of a benzene ring in the above polymer compound are preferably substituted with any one of —COOH, —COOR, and —COO⁻M.

Further, a block polymer of the present invention contains at least one block segment having a glass transition point (Tg) of preferably 30° C. or lower.

The block segment has a glass transition point of more preferably 20° C. or lower, furthermore preferably 10° C. or lower.

A low glass transition point improves fluidity of a polymer when a polymer-containing composition described below is provided on a medium and facilitates coating of a functional substance in the composition with the polymer. Thus, weatherability or the like of the functional substance improves.

The present invention has such a feature that the repeating unit of the polymer compound includes a repeating unit containing a substituent composed of an aromatic polycarboxylic acid derivative represented by the general formula (2). The presence of a plurality of carboxylic acid units increases an ion concentration and is very useful for providing a functional polymer material as a polymer compound having an alkenyl ether repeating unit structure with low viscosity and good dispersibility.

A content of the polyalkenyl ether structure is preferably 50 mol % or more, and the polymer compound more preferably has a repeating unit structure of the polyalkenyl ether structure in a main chain. When a content of the polyalkenyl ether structure is less than 50 mol %, fixing property may be insufficient. A polymer compound having a polyalkenyl ether structure in a main chain generally has a low glass transition point (Tg) and has flexible molecular mobility. A block polymer preferably has more flexible molecular mobility for improving dispersion stability and inclusion property because the molecules of the block polymer physically entangle with a surface of the functional substance resulting in high affinity. Further, the block polymer preferably has flexible molecular mobility because a coating layer is easily formed on a recording medium as described below. The main chain of the block polymer has a glass transition temperature (Tg) of preferably 30° C. or lower, more preferably 20° C. or lower, furthermore preferably 10° C. or lower.

Further, the polymer compound of the present invention has such a feature that the compound has at least two block segments and a repeating unit structure represented by the general formula (2) in at least one block segment.

A preferable embodiment of the block polymer compound of the present invention is an amphipathic block polymer compound. Amphipathic property refers to property having lyophilicity and lyophobicity, and the amphipathic block polymer compound refers to a polymer compound having at least one lyophilic block segment and at least one lyophobic block segment. The lyophilicity refers to property of having high affinity with a solvent mainly used in a polymer-containing composition described below, and the lyophobicity refers to property of having low affinity with the solvent. The solvent is preferably water, and the block polymer compound of the present invention preferably has at least one hydrophilic block segment and at least one hydrophobic block segment.

Amphipathic property develops in the block polymer compound of the present invention having at least one hydrophobic block segment and at least one hydrophilic block segment. Hydrophilicity refers to property of having high affinity with water and being easily dissolved in water, and hydrophobicity refers to property of having low affinity with water and being hardly dissolved in water. Examples of the hydrophilic block include a block segment having a repeating unit structure containing a hydrophilic unit such as a carboxylic acid or a carboxylate salt represented by the general formula (2) or the like. Specific examples thereof include: a structure in which $R^1$ in the repeating unit structure represented by the general formula (2) is represented by —COOH or —COO⁻M; a structure containing many hydrophilic oxyethylene units; and a structure having a hydroxyl group or the like. However, the hydrophilic block in the block polymer compound of the present invention is not limited thereto.

Examples of the hydrophobic block include a block segment having a repeating unit structure containing a hydrophobic unit such as an isobutyl group, a t-butyl group, a phenyl group, a biphenyl group, or a naphthyl group. Specific examples thereof include a block segment having a hydrophobic monomer such as styrene or t-butyl methacrylate as a repeating unit, and preferable examples thereof include a block segment having a repeating unit structure of a polyalkenyl ether structure. Specific examples of thereof include: a repeating unit structure represented by the general formula (2) in which $R^1$ is represented by —COOR⁴; and a repeating structure represented by the following general formula (8). However, the hydrophobic block in the block polymer compound of the present invention is not limited thereto.

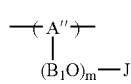

(8)

(In the formula: A" represents an alkenyl ether group which may be substituted; $B_1$ represents a linear or branched alkylene group having 1 to 15 carbon atoms which may be substituted; m represents an integer from 0 to 30; when m is larger than 1, $B_1$ may be different from each other; J represents any one of a linear or branched alkyl group having 3 to 15 carbon atoms which may substituted, an aromatic ring which may be substituted, a condensed ring which may be substituted, and a structure formed by bonding through single bonds at most three aromatic rings which may be substituted.)

In the general formula (8), A" represents a polyalkenyl ether group which may be substituted. An alkylene group in the polyalkenyl ether group may be substituted with a linear or branched alkylene group having 1 to 5 carbon atoms or with a halogen atom.

$B_1$ represents a linear or branched alkylene group having 1 to 15 carbon atoms which may be substituted. Examples of the substituent to the alkylene group include ethylene, propylene, and butylene.

m represents an integer from 0 to 30, preferably from 1 to 10. When m is larger than 1, $B_1$ may be different from each other.

J represents any one of a linear or branched alkyl group having 3 to 15 carbon atoms which may substituted, an aromatic ring which may be substituted, a condensed ring which may be substituted, and a structure formed by bonding through single bonds at most three aromatic rings which may be substituted. Examples of the alkyl group include a propyl group, an isopropyl group, a butyl group, and a t-butyl group. Examples of the aromatic ring structure include a phenyl group, a naphthyl group, a pyridyl group, and a biphenyl group. Examples of the substituent include an alkyl group and an alkoxy group.

Specific examples of the repeating unit structure of the hydrophobic block include the following but are not limited thereto.

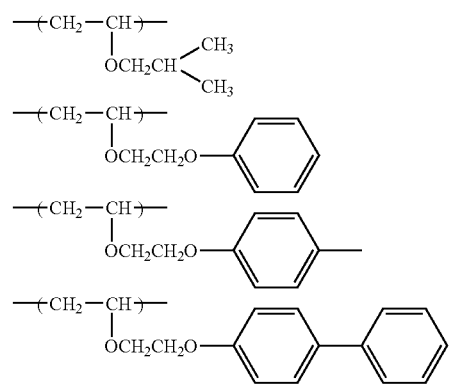

Further, each block segment in the block polymer compound of the present invention may be composed of repeating units derived from a single monomer or repeating units derived from a plurality of monomers. Examples of the block segment having the repeating units derived from a plurality of monomers include a random copolymer and a gradient copolymer having a gradually changing composition ratio. The block polymer compound of the present invention may be a polymer having the above-mentioned block polymer grafted to another polymer.

In the present invention, a content of the repeating unit structure represented by the general formula (1) in the block polymer compound is desirably in the range of 0.01 to 99 mol %, preferably 1 to 90 mol % with respect to the total block polymer compound. A content of less than 0.01 mol % may deteriorate the dispersion stability, and a content of more than 99 mol % is not preferable because a structure effectively including a functional substance is hardly formed.

The polymer compound of the present invention has a number average molecular weight (Mn) of 400 or more and 10,000,000 or less, preferably 1,000 or more and 1,000,000 or less. A number average molecular weight of larger than 10,000,000 results in excessive entanglement within a polymer chain and between the polymer chains, inhibiting dispersion of the polymer compound in a solvent. A number average molecular weight of less than 400 may inhibit a steric effect as a polymer because of a small molecular weight. Each block segment independently has a polymerization degree of preferably 2 or more and 10,000 or less, more preferably 2 or more and 5,000 or less, furthermore preferably 2 or more and 4,000 or less.

The polymer compound of the present invention is often polymerized through mainly cationic polymerization. Examples of a polymerization initiator include proton acids such as hydrochloric acid, sulfuric acid, methanesulfonic acid, trifluoroacetic acid, trifluoromethanesulfonic acid, and perchloric acid or combinations of Lewis acids such as $BF_3$, $AlCl_3$, $TiCl_4$, $SnCl_4$, $FeCl_3$, $RAlCl_2$, and $R_{1.5}AlCl_{1.5}$ (R represents alkyl) with a cationogen (examples of the cationogen include proton acids and adducts of carboxylic acids with water, alcohol, and vinyl ether). The presence of such a polymerization initiator with a polymerizable compound (monomer) causes a polymerization reaction to proceed, to thereby synthesize a polymer compound.

A polymerization method more preferably employed in the present invention will be described. A synthesis method for a polymer having a polyvinyl ether structure has been reported, and a typical example thereof involves a method through cation living polymerization reported by Aoshima et al. (Polymer Bulletin, 15, 417, 1986; Japanese Patent Application Laid-Open No. H11-322942). Polymer synthesis through cation living polymerization enables synthesis of various polymers such as a homopolymer, a copolymer composed of two or more monomers, a block polymer, a graft polymer, and a gradient polymer with the precisely same length (molecular weight). Living polymerization can be carried out in an HI/I$_2$ system, an HCl/SnCl$_4$ system, or the like.

The block polymer compound preferably used in the present invention has a block segment having a repeating unit structure containing a carboxylic acid, a carboxylate ester, or a carboxylate salt bonded through a connecting group, not directly bonded to a main chain of the polymer. Thus, the block polymer compound can exhibit suitable interaction for forming a superstructure or a highly stable dispersion. The block polymer compound having two or more block segments can exhibit two or more functions. Thus, a finer superstructure compared to a polymer compound having two or less block segments can be formed. A plurality of block segments may have similar properties, to thereby stabilize the property.

A first aspect of the present invention has such a feature that a polymer compound has a repeating unit structure represented by the above general formula (2), and that a plurality of carboxylic acids, carboxylate esters, or carboxylate salts are present in the repeating unit structure. For example, use of a block polymer of a preferable embodiment of the present invention for a polymer-containing composition described below increases the ion concentration in a carboxylate salt, particularly compared to that in a monocarboxylate salt, thereby providing a composition having higher dispersion stability.

The present invention has such a feature that the repeating unit of the block polymer having three or more block segments includes a repeating unit containing a substituent composed of a polycarboxylic acid derivative represented by the general formula (2). Inclusion of three or more block segments allows separation of many functions, and the presence of a plurality of carboxylic acid units increases the ion concentration. Thus, the block polymer is very useful for providing a functional polymer material as a polymer compound having a vinyl ether repeating unit structure with low viscosity and good dispersibility.

Hereinafter, a polymer compound in which an ABC-type triblock polymer composed of three different block segments has a hydrophobic block segment in an A block, a nonionic hydrophilic block segment in a B block, and a repeating unit structure represented by the above general formula (2) in a C block will be described.

Examples of the hydrophobic block segment corresponding to the A block desirably include specific examples of the above-mentioned hydrophobic block. Examples of the nonionic hydrophilic block segment corresponding to the B block include block segments each having a repeating unit structure containing a substituent such as a hydroxyl group or a side chain such as a polyoxyethylene chain. A specific example thereof includes a block segment containing a monomer of polyvinyl alcohol or the like as a repeating unit, and a preferable specific example thereof includes a block segment having a repeating unit structure composed of a polyalkenyl ether structure. Specific examples of the repeating unit structure include a repeating unit structure represented by the following general formula (5). However, the nonionic hydrophilic block in the polymer compound of the present invention is not limited thereto.

(In the formula: A" represents a polyalkenyl ether group which may be substituted; B" represents a linear or branched alkylene group having 1 to 5 carbon atoms which may be substituted; m represents an integer from 0 to 30; when m is larger than 1, B" may be different from each other; D" represents a single bond or a linear or branched alkylene group having 1 to 5 carbon atoms which may be substituted; K represents any one of a linear or branched alkyl group having 1 to 3 carbon atoms which may be substituted and a hydroxyl group.)

In the general formula (5), A" represents a polyalkenyl ether group which may be substituted. An alkenyl group in the polyalkenyl ether group may be substituted with a linear or branched alkyl group having 1 to 5 carbon atoms or with a halogen atom.

B" represents a linear or branched alkylene group having 1 to 5 carbon atoms which may be substituted, preferably a linear alkylene group having 1 to 2 carbon atoms. Examples of the substituent to the alkylene group include methylene, ethylene, and propylene.

m represents an integer from 0 to 30, preferably from 1 to 10. When m is larger than 1, B" may be different from each other.

D" represents a single bond or a linear or branched alkylene group having 1 to 5 carbon atoms which may be substituted. Examples of the alkylene group include methylene, ethylene, and propylene.

K represents any one of a linear or branched alkyl group having 1 to 3 carbon atoms which may be substituted and a hydroxyl group. Examples of the alkyl group include a methyl group, an ethyl group, and a propyl group.

The repeating unit structure represented by the general formula (5) exhibits hydrophilicity. Thus, the above-mentioned structure as a unit may be hydrophilic such as an oxyethylene group or a hydroxyl group, or hydrophobic such as an oxypropylene group, an ethyl group, or a propyl group. In this case, the repeating unit structure must be entirely hydrophilic. For example, when K is a propyl group, (B"O)$_m$ is a relatively long oxyethylene group, and when K is a hydroxyl group, (B"O)$_m$ is an oxypropylene group. Specific examples of the repeating unit structure in the nonionic hydrophilic block include the following, but are not limited thereto.

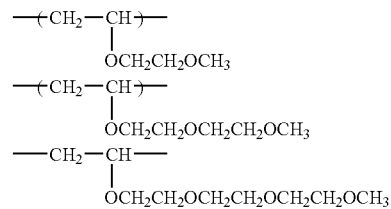

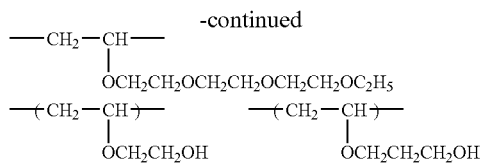

The polymer compound contains polycarboxylic acid having a plurality of carboxylic acid groups such as a dicarboxylic acid, or a polycarboxylic acid derivative including: a polycarboxylate ester such as methyl polycarboxylate, ethyl polycarboxylate, or propyl polycarboxylate; or a carboxylate salt such as sodium polycarboxylate, potassium polycarboxylate, or ammonium polycarboxylate on a side chain of the C segment. A polycarboxylic acid has such a feature that the ion concentration increases compared to that of monocarboxylic acid because a plurality of carboxylic acid groups are present. Dispersion of the compound of the present invention in a solvent having high dielectic constant such as water is very useful because a structure derived from a polymer such as a micelle due to ion repulsion or the like increases in stability.

The polymer compound preferably contains an aromatic polycarboxylic acid derivative in which a carboxylic acid group is bonded with an aromatic carbon on a side chain of the C segment. In this case, a more preferable embodiment of the polymer compound has two functional groups in the carboxylic acid derivative, which are each preferably bonded to meta-positions.

A polymer compound in which an ABC-type triblock polymer composed of three different block segments has a hydrophilic or hydrophobic block segment in the A block, a hydrophobic block segment in the B block, and a repeating unit structure represented by the above general formula (2) in the C block will be described.

The block polymer compound of the present invention may contain a segment causing a phase change from hydrophilic to hydrophobic, or hydrophobic to hydrophilic by responding to stimuli such as temperature change, exposure to an electromagnetic wave, pH change, and concentration change. The block polymer compound of the present invention is a block polymer having at least three block segments. The block polymer compound has block segments A, B, and C in the order and has a block segment containing at least one selected from a polycarboxylic acid, a polycarboxylate ester, and a polycarboxylate salt on a side chain of the C segment. One block segment may include a stimuli-responsive block segment. The stimulus is preferably one of temperature change, exposure to an electromagnetic wave, pH change, and concentration change, and may be a combination thereof. Specific examples of a stimuli-responsive block polymer compound of the present invention include, but are not limited to, an ABC triblock polymer composed of:

a stimuli-responsive repeating unit in the hydrophobic or hydrophilic A segment:

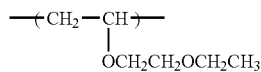

a repeating unit in the hydrophobic B segment:

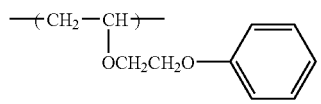

a repeating unit having a sulfonic acid on a side chain of the C segment:

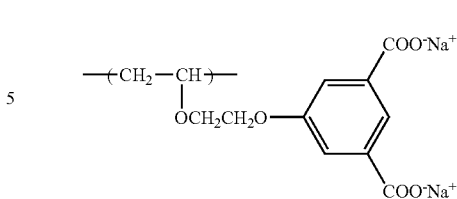

The hydrophilic A segment is a block segment which responds to stimulus of temperature, and may be used as a hydrophobic segment at about 20° C. or higher and as a hydrophilic segment at about 20° C. or lower.

Each block segment in the block polymer compound of the present invention may be composed of repeating units derived from a single monomer, or repeating units derived from a plurality of monomers. Examples of the block segment having the repeating units derived from a plurality of monomers include a random copolymer and a gradient copolymer having a gradually changing composition ratio. The block polymer compound of the present invention may be a polymer having the above-mentioned block polymer grafted to another polymer. Further, the block polymer compound of the present invention is a block polymer compound having three or more block segments. Examples of a block structure include: a triblock polymer having different block segments A, B, and C; and a structure having such a triblock structure and another polymer unit bonded thereto. Further examples thereof include: a block polymer having four different block segments A, B, C, and D; a block polymer having block segments A, B, C, and A; and a block polymer having 5 or more block segments. The block polymer compound of the present invention has such a feature that the compound has at least three block segments.

Further, the present invention relates to a polymer compound containing a copolymer composition composed of a repeating unit structure containing a polycarboxylic acid on a side chain, the repeating unit structure being represented by the general formula (2), and a repeating unit structure containing a monocarboxylic acid on a side chain, the repeating unit structure being represented by the following general formula (9).

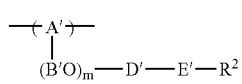

In the general formula (9), A' represents a polyalkenyl ether group which may be substituted. The polyalkenyl group may be substituted with a linear or branched alkyl group having 1 to 5 carbon atoms or with a halogen atom.

$B^1$ represents a linear or branched alkylene group having 1 to 15 carbon atoms which may be substituted. Examples of a substituent to the alkylene group include ethylene, propylene, and butylene.

m represents an integer from 0 to 30, preferably from 1 to 10. When m is an integer larger than 1, B' may be different from each other.

D' represents a single bond or a linear or branched alkylene group having 1 to 10 carbon atoms which may be substituted. Examples of the alkylene group include methylene, ethylene, propylene, butylene, pentylene, hexylene, heptylene, and octylene.

E' represents any one of an aromatic ring which may be substituted, a condensed ring which may be substituted, a structure formed by bonding through single bonds at most three aromatic rings which may be substituted, and a methylene group. Examples of the aromatic ring structure include phenyl, pyridylene, pyrimidyl, naphthyl, anthranyl, phenanthrenyl, thiophenyl, and furanyl.

$R^2$ represents any one of —COOH, —COOR$^3$, and —COO$^-$M. $R^3$ represents a linear or branched alkyl group having 1 to 5 carbon atoms which may be substituted or an aromatic ring which may be substituted. Examples of the aromatic ring structure include a phenyl group, a pyridyl group, and a biphenyl group. Examples of the substituent include an alkyl group and an alkoxy group. M represents a monovalent or polyvalent metal cation. Specific examples of M include: monovalent metal cations such as sodium, potassium, and lithium; and polyvalent metal cations such as magnesium, calcium, nickel, and iron. When M represents a polyvalent metal cation, M forms a counter ion with two or more COO$^-$ anions.

A hydrogen atom in the aromatic ring or in the methylene group, which is not substituted with $R^2$, may be substituted. Examples of the substituent include an alkyl group, an alkoxy group, and a halogen atom.

Specific examples of the repeating unit structure represented by the general formula (9) include the following structures.

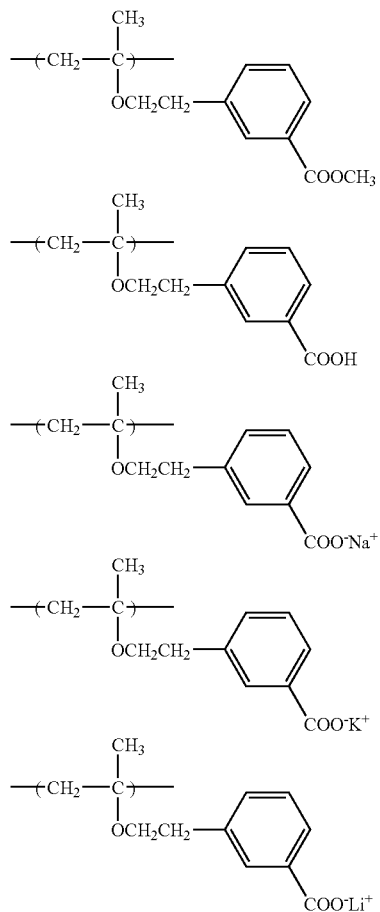

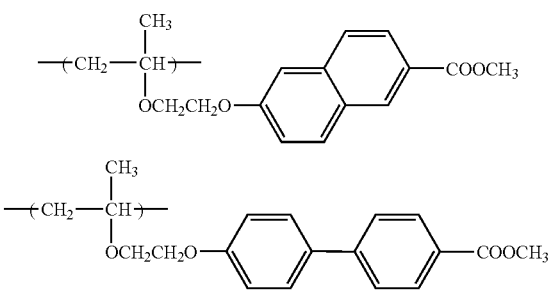

Preferable specific examples of the repeating unit structure include the following.

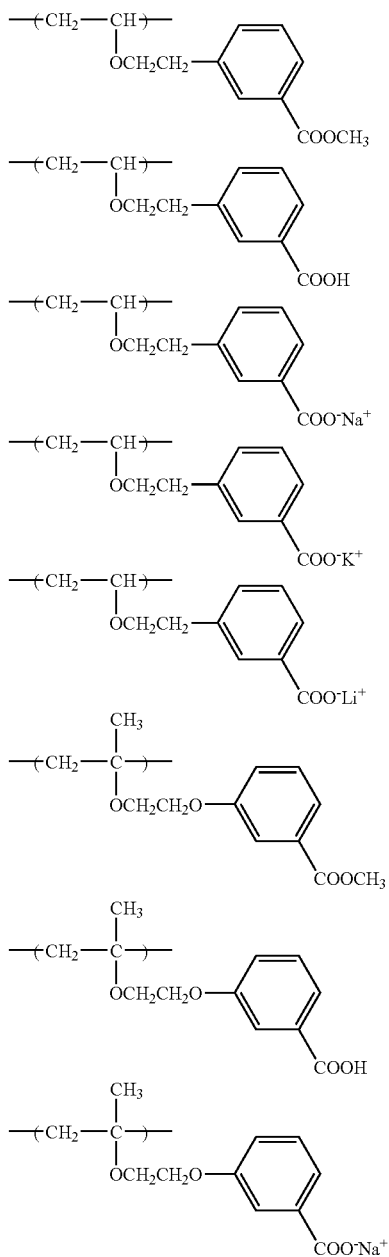

-continued

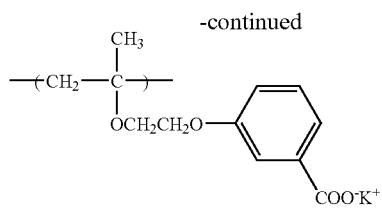

More preferable specific examples of the repeating unit structure include the following.

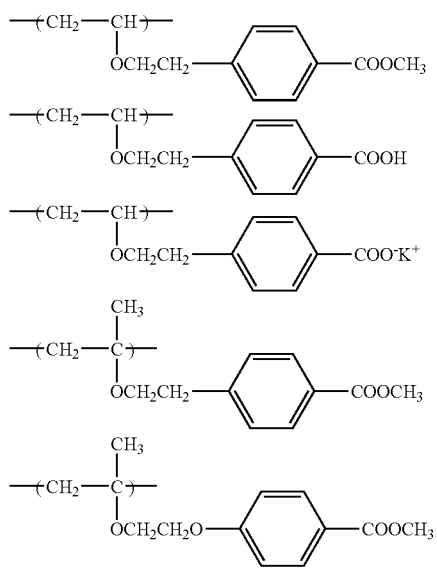

The present invention has such a feature that the polymer compound includes a copolymer composition composed of a repeating unit structure containing a polycarboxylic acid group on a side chain, the repeating unit structure being represented by the general formula (2), and a repeating unit structure containing a monocarboxylic acid group on a side chain, the repeating unit structure being represented by the general formula (9). Examples of the copolymer composition may include: a random copolymer composition in which two types of repeating unit structures are randomly arranged; an alternating copolymer composition in which two types of repeating unit structures are alternatively arranged; a gradient copolymer composition having a gradually changing composition ratio of two types of repeating unit structures; and a copolymer composition close to a block copolymer composition. Inclusion of such a copolymer composition composed of a monocarboxylic acid and a polycarboxylic acid allows control of the ion concentration by means of carboxylic anions.

Further, compared to a monocarboxylic acid-containing polymer, a polycarboxylic acid-containing polymer has high ion concentration, high dispersion stability when a functional substance is dispersed therein, and high ejection stability as an ink composition as described below. Meanwhile, the polycarboxylic acid-containing polymer may increase in viscosity at low pH with increasing ion concentration because dissociation of carboxylic acid is suppressed, compared to a polymer-containing composition including a monocarboxylic acid-containing polymer. Thus, copolymerization of these polymer results in a polymer compound having a vinyl ether repeating unit structure, which allows control of the dispersion stability or viscosity in various pH ranges of the polymer-containing compound, and thus is very useful for controlling the dispersion stability, ejection performance, and ink viscosity of an ink composition used as an ink jet ink.

Preferable specific examples of the repeating unit structure represented by the general formula (10) include the following structures.

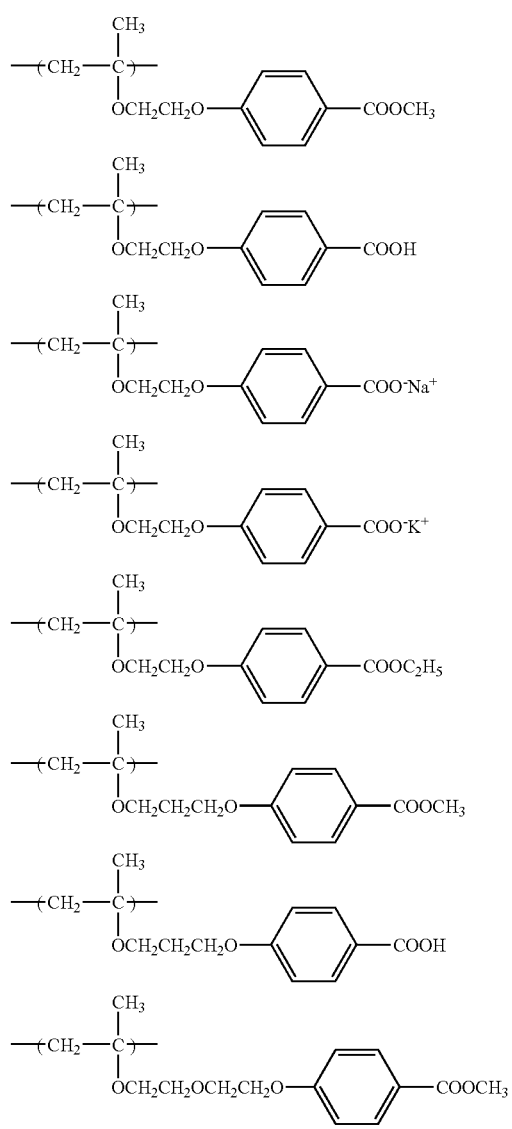

More preferable specific examples of the repeating unit structure include the following repeating unit structures.

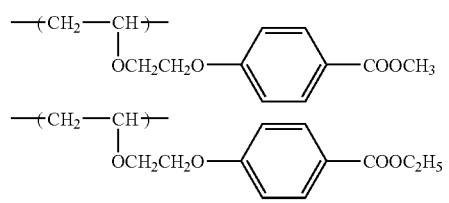

-continued

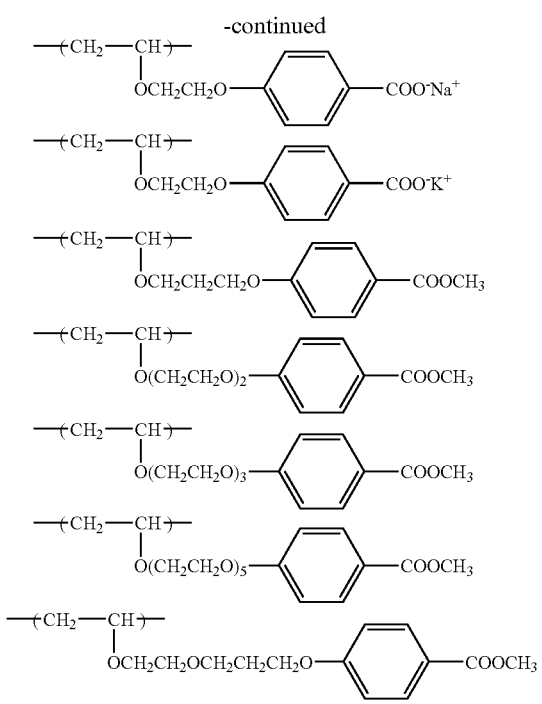

Further, the polymer compound of the present invention contains repeating units derived from a plurality of monomers. Examples of a copolymer segment containing the repeating units derived from a plurality of monomers include a random copolymer, an alternating copolymer, a block copolymer, and a gradient copolymer having a gradually changing composition ratio. The polymer compound of the present invention may be a polymer having the above-mentioned copolymer grafted to another polymer.

The present invention also relates to a composition containing the above-described polymer compound of the present invention.

The composition of the present invention preferably contains the above-mentioned polymer compound, a colorant, and a functional substance exhibiting a predetermined useful function. The polymer compound may be suitably used for dispersing the colorant, the functional substance, or the like well. Examples of the functional substance include: colorants such as a pigment and a dye; metals; herbicides; insecticides; and biomaterials such as a drug. The polymer compound of the present invention may be used as a water-soluble polymer compound, an adhesive, a pressure sensitive adhesive, or the like, and thus the functional substance need not be present.

The amount of the functional substance in the composition of the present invention is preferably 0.1 to 50 mass % with respect to the mass of the composition of the present invention. The functional substance may be a soluble substance and may include a dye and a molecular catalyst.

The amount of the polymer compound in the composition of the present invention is preferably 0.5 to 98 mass % with respect to the mass of the composition of the present invention.

Examples of the composition of the present invention include a recording material containing a solvent or dispersing medium, a colorant, and the above-mentioned polymer compound.

A specific example of the recording material includes a toner composition containing a dispersing medium such as a binder resin, a colorant, and the above-mentioned polymer compound.

Further, another specific example thereof includes an ink composition containing a solvent, a colorant, and the above-mentioned polymer compound.

Hereinafter, the ink composition as a preferable embodiment of the present invention will be described.

The content of the above-mentioned polymer compound in the ink composition of the present invention falls within the range of 0.1 mass % or more and 90 mass % or less, preferably 1 mass % or more and 80 mass % or less. The content thereof preferably falls within the range of 1 mass % or more and 30 mass % or less for an ink jet printer.

Next, components other than the above-mentioned polymer compound in the ink composition of the present invention will be described in detail. Other components include an organic solvent, water, an aqueous solvent, a colorant, and an additive.

[Organic Solvent]

Examples of the organic solvent include a hydrocarbon-based solvent, an aromatic solvent, an ether-based solvent, a ketone-based solvent, an ester-based solvent, and an amide-based solvent.

[Water]

Water used in the present invention is preferably an ion-exchanged water, purified water, and ultrapure water from which metal ions and the like are removed.

[Aqueous Solvent]

Examples of the aqueous solvent include: polyhydric alcohols such as ethylene glycol, diethylene glycol, triethylene glycol, polyethylene glycol, propylene glycol, polypropylene glycol, and glycerin; polyhydric alcohol ethers such as ethylene glycol monomethyl ether, ethylene glycol monoethyl ether, ethylene glycol monobutyl ether, diethylene glycol monoethyl ether, and diethylene glycol monobutyl ether; and nitrogen-containing solvents such as N-methyl-2-pyrrolidone, substituted pyrrolidone, and triethanolamine. Further, monohydric alcohols such as methanol, ethanol, and isopropyl alcohol may be used for the purpose of accelerating drying of an aqueous dispersed substance on a recording medium.

The content of the organic solvent, water, and aqueous solvent in the ink composition of the present invention falls within the range of preferably 20 to 95 mass %, more preferably 30 to 90 mass % with respect to the total mass of the ink composition.

[Colorant]

The ink composition of the present invention contains a colorant such as a pigment or a dye, and preferably contains a pigment.

Hereinafter, specific examples of the pigment and the dye used in the ink composition will be described.

The pigment may be an organic pigment or an inorganic pigment, and a black pigment and three primary color pigments of cyan, magenta, and yellow can preferably be used as a pigment for an ink. Pigments of colors excluding the above-mentioned colors, colorless or light colored pigments, metallic luster pigments, and the like may also be used. A novel pigment synthesized for the present invention may also be used.

Examples of commercially available pigments of black, cyan, magenta, and yellow are given below.

Examples of the black pigment include, but are not limited to: Raven1060 (trade name, available from Columbian Carbon Co., Ltd.); MOGUL-L (trade name, available from Cabot Corporation).; Color Black FW1 (trade name, available from Degussa Co., Ltd.); and MA100 (trade name, available from Mitsubishi Chemical Corporation).

Examples of the cyan pigment include, but are not limited to: C.I. Pigment Blue-15:3; C.I. Pigment Blue-15:4; and C.I. Pigment Blue-16.

Examples of the magenta pigment include, but are not limited to: C.I. Pigment Red-122; C.I. Pigment Red-123; and C.I. Pigment Red-146.

Examples of the yellow pigment include, but are not limited to: C.I. Pigment Yellow-74; C.I. Pigment Yellow-128; and C.I. Pigment Yellow 129.

The ink composition of the present invention may employ a pigment which is self-dispersible in water. Examples of the self-dispersible pigment include: a pigment having a polymer adsorbed on a surface thereof utilizing a steric hindrance effect; and a pigment utilizing electrostatic repulsion. Examples of a commercially available self-dispersible pigment include: CAB-O-JET200, CAB-O-JET300 (trade names, available from Cabot Corporation); and Microjet Black CW-1 (trade name, available from Orient Chemical Industries, Ltd.).

The pigment in the ink composition of the present invention is preferably used in an amount of 0.1 to 50 mass % with respect to the mass of the ink composition. An amount of the pigment of 0.1 mass % or more provides a preferable image density, and an amount of the pigment of 50 mass % or less provides preferable dispersibility of the pigment. The pigment is more preferably used in an amount of 0.5 to 30 mass %.

The ink composition of the present invention may also employ a dye. Examples of the dye that can be used include a direct dye, an acid dye, a basic dye, a reactive dye, a water-soluble dye of a food coloring matter, an oil-soluble dye, and a disperse dye of an insoluble coloring matter.

Examples of the water-soluble dye include: direct dyes such as C.I. Direct Black-17, -62, and -154, C.I. Direct Yellow-12, -87, and -142, C.I. Direct Red-1, -62, and -243, C.I. Direct Blue-6, -78, and -199, C.I. Direct Orange-34 and -60, C.I. Direct Violet-47 and -48, C.I. Direct Brown -109, and C.I. Direct Green-59; acid dyes such as C.I. Acid Black-2, -52, and -208, C.I. Acid Yellow-11, -29, and -71, C.I. Acid Red-1, -52, and -317, C.I. Acid Blue-9, -93, and -254, C.I. Orange-7 and -19, and C.I. Acid Violet-49; reactive dyes such as C.I. Reactive Black-1, -23, and -39, C.I. Reactive Yellow-2, -77, and -163, C.I. Reactive Red-3, -111, and -221, C.I. Reactive Blue-2, -101, and -217, C.I. Reactive Orange-5, -74, and -99, C.I. Reactive Violet-1, -24, and -38, C.I. Reactive Green-5, -15, and -23, and C.I. Reactive Brown-2, -18, and -33; C.I. Basic Black-2; C.I. Basic Red-1, -12, and -27; C.I. Basic Blue-1 and -24; C.I. Basic Violet-7, -14, and -27; and C.I. Food Black-1 and -2.

Commercially available oil-soluble dyes of respective colors will be exemplified below.

Examples of a black oil-soluble dye include, but are not limited to, C.I. Solvent Black-3, -22:1, and -50.

Examples of a yellow oil-soluble dye include, but are not limited to, C.I. Solvent Yellow-1, -25:1, and -172.

Examples of an orange oil-soluble dye include, but are not limited to, C.I. Solvent Orange-1, -40:1, and -99.

Examples of a red oil-soluble dye include, but are not limited to, C.I. Solvent Red-1, -111, and -229.

Examples of a violet oil-soluble dye include, but are not limited to, C.I. Solvent Violet-2, -11, and -47.

Examples of a blue oil-soluble dye include, but are not limited to, C.I. Solvent Blue-9, -43, and -134.

Examples of a green oil-soluble dye include, but are not limited to, C.I. Solvent Green-1, -20, and -33.

Examples of a brown oil-soluble dye include, but are not limited to, C.I. Solvent Brown-1, -12, and -58.

The above-mentioned examples of the colorant are preferable for the ink composition of the present invention, but the colorant used for the ink composition of the present invention is not particularly limited to the above-mentioned colorants. The dye in the ink composition of the present invention is preferably used in an amount of 0.1 to 50 mass % with respect to the mass of the ink.

[Additive]

Various additives, auxiliaries, and the like can be added to the composition of the present invention as required. An example of the additives is a dispersion stabilizer for stably dispersing a pigment in a solvent. The composition of the present invention contains a polymer having a polyvinyl ether structure and thus has a function of dispersing a particulate solid such as a pigment, but another dispersion stabilizer may be added when the dispersion is insufficient.

A resin or surfactant each having both hydrophilic and hydrophobic portions can be used as the other dispersion stabilizer. Examples of the resin having both hydrophilic and hydrophobic portions include a copolymer of a hydrophilic monomer and a hydrophobic monomer.

Examples of the hydrophilic monomer include acrylic acid, methacrylic acid, maleic acid, fumaric acid, the above-mentioned monocarboxylate esters, vinyl sulfonate, styrene sulfonate, vinyl alcohol, acrylamide, and methacryloxyethyl phosphate. Examples of the hydrophobic monomer include styrene, a styrene derivative such as α-methylstyrene, vinylcyclohexane, a vinylnaphthalene derivative, acrylate esters, and methacrylate esters. The copolymer may have various structures such as a random copolymer, a block copolymer, and a graft copolymer. The hydrophilic monomer and the hydrophobic monomer are not limited to those described above.

Examples of the surfactant that can be used include an anionic surfactant, a nonionic surfactant, a cationic surfactant, and an amphoteric surfactant. Examples of the anionic surfactant include a fatty acid salt, alkyl sulfate, alkylaryl sulfonate, alkyldiaryl ether disulfonate, dialkylsulfosuccinate, alkylphosphate, a naphthalenesulfonic acid-formalin condensate, polyoxyethylene alkylphosphate, and a glycerol borate fatty ester. Examples of the nonionic surfactant include polyoxyethylene alkyl ether, a polyoxyethylene oxy propylene block copolymer, a sorbitan fatty ester, a glycerin fatty ester, a polyoxyethylene fatty ester, polyoxyethylene alkylamine, a fluorine-based surfactant, and a silicon-based surfactant. Examples of the cationic surfactant include an alkylamine salt, a quaternary ammonium salt, an alkylpyridinium salt, and an alkylimidazolium salt. Examples of the amphoteric surfactant include alkyl betaine, alkylamine oxide, and phosphatidylcholine. The surfactant is also not limited to those described above.

An aqueous solvent can be added to the composition of the present invention as required. When the composition is used for an ink-jet ink, the aqueous solvent is used to prevent drying and solidification of the ink in a nozzle portion, and may be used alone or as a mixture. Examples of the aqueous solvent include those described above. The content of the aqueous solvent in the ink falls within the range of 0.1 to 60 mass %, preferably 1 to 40 mass % with respect to the total mass of the ink.

Examples of another additive that can be added when the composition is used as an ink include: a pH adjustor for stabilizing the ink and securing stability of the ink with a flow path of a recording apparatus; a penetrating agent for accelerating penetration of the ink into a recording medium and for accelerating apparent drying; a fungicide for preventing formation of molds in the ink; a chelating agent for sealing metal ions in the ink and for preventing metal deposits in a nozzle portion, deposits of insoluble substances in the ink, or the like; an anti-foaming agent for preventing formation of bubbles during circulation or migration of a recording liquid or in production of the recording liquid; an antioxidant; a fungicide; a viscosity modifier; a conductor; and a UV absorber.

The ink composition of the present invention can be prepared by mixing the above-mentioned components and uniformly dissolving or dispersing the mixture. That is, the ink composition can be prepared by: mixing a plurality of components; pulverizing and dispersing the mixture using a sand mill, a ball mill, a homogenizer, a nanomizer, or the like to prepare an ink mother liquor; and adding a solvent or an additive to the ink mother liquor to adjust the physical properties.

Next, the toner composition of the present invention will be described. The toner composition specifically contains a dispersing medium such as a binder resin, a colorant, and a polymer compound having the repeating unit structure represented by the above general formula (2) or (3).

The content of the polymer compound having the repeating unit structure represented by the above general formula (2) or (3) in the toner composition of the present invention falls within the range of 0.1 mass % or more and 95 mass % or less, preferably 0.5 mass % or more and 80 mass % or less.

The polymer compound of the present invention can be used as a binder resin itself, or can be used in combination with a binder resin such as a styrene-acrylate resin or a polyester resin.

Next, components in the toner composition of the present invention other than the polymer compound will be described in detail. Other components include a binder resin, a colorant (pigment, dye), a charge regulator, a releasing agent, an external additive, and magnetic particles.

(Addition of Other Components of Toner Composition)

Examples of the binder resin include a styrene-acrylate copolymer, polyester, and polycarbonate. The binder resin is preferably used in an amount of 10 mass % or more and 99 mass % or less. Each of the pigments or dyes in the above-mentioned description of the ink composition can be used as the colorant. The colorant is used in an amount of 0.1 mass % or more and 50 mass % or less. Examples of the charge regulator include a metal-azo complex, a triphenylmethane dye, nigrosine, and an ammonium salt. The charge regulator is used in an amount of 0.1 mass % or more and 30 mass % or less. Examples of the releasing agent include synthetic wax and natural wax. Examples of the external additive include: inorganic fine particles such as silica, alumina, and titania; and resin fine particles such as polyvinylidene fluoride (PVDF) and polytetrafluoroethylene. Examples of the magnetic particles include magnetite, hematite, and ferrite. The toner composition need not contain the above-mentioned components to function or may contain components not described above.

A method of preparing the toner composition of the present invention involves, for example: mixing, melting, and kneading the above-mentioned components to prepare a uniform mixture; pulverizing the mixture using a speed mill or a jet mill; classifying the pulverized product to obtain a toner having a desired size; adding an external additive to the toner; and mixing the whole using a mixer.

Next, an image forming method, a liquid applying method, and an image forming apparatus each using the composition of the present invention will be described.

[Image Forming Method, Liquid Applying Method, and Image Forming Apparatus]

The composition of the present invention can be used for various image forming methods such as various printing methods, ink jet methods, and electrophotographic methods and apparatuses therefore, and an image can be drawn by means of an image forming method using such an apparatus. In addition, when a liquid composition is used, in the ink jet method or the like, the composition of the present invention can be used for a liquid applying method for forming a fine pattern or for administering a drug.

The image forming method of the present invention is a method of performing excellent image formation by using the composition of the present invention. The image forming method of the present invention is preferably an image forming method involving: ejecting an ink composition of the present invention from an ink ejection portion; and applying the ink composition on a recording medium to perform recording. The image formation preferably employs a method using the ink jet method involving allowing heat energy to act on an ink to eject the ink.

An ink jet printer using the ink composition for ink jet of the present invention is applicable to various ink jet recording apparatuses such as a piezo-ink jet type printer using a piezoelectric element and a bubble jet (registered trademark) type printer that performs recording by allowing heat energy to act on an ink to bubble the ink.

Hereinafter, the outline of the ink jet recording apparatus will be described with reference to FIG. 1. However, FIG. 1 shows only an example of the structure, and does not limit the present invention.

FIG. 1 is a block diagram showing the structure of an ink jet recording apparatus.

FIG. 1 shows the case where a head is moved to perform recording on a recording medium. In FIG. 1, an X-direction drive motor 56 and a Y-direction drive motor 58 for driving a head 70 in the X and Y directions are connected to a CPU 50 that controls the overall operation of the production apparatus via an X-motor drive circuit 52 and a Y-motor drive circuit 54. The X-direction drive motor 56 and the Y-direction drive motor 58 are driven in accordance with an instruction from the CPU via the X-motor drive circuit 52 and the Y-motor drive circuit 54, whereby the position of the head 70 with respect to the recording medium is determined.

As shown in FIG. 1, not only the X-direction drive motor 56 and the Y-direction drive motor 58 but also a head drive circuit 60 is connected to the head 70. The CPU 50 controls the head drive circuit 60 to drive the head 70, that is, to perform ejection of the ink-jet ink or the like. Furthermore, an X-encoder 62 and a Y-encoder 64 for detecting the position of the head are connected to the CPU 50, and position information of the head 70 is inputted to the CPU 50. A control program is also inputted into a program memory 66. The CPU 50 allows the head 70 to move on the basis of the control program and the position information from the X-encoder 62 and the Y-encoder 64, to thereby place the head at a desired position on the recording medium, followed by ejection of the ink-jet ink. Thus, a desired image can be drawn on the recording medium. In addition, in the case of an image recording apparatus into which a plurality of ink-jet inks can be charged, an operation such as that described above is performed on each ink-jet ink a predetermined number of times, whereby a desired image can be drawn on the recording medium.

It is also possible that, after the ink-jet ink has been ejected, as required, the head 70 be moved to a position where removing means (not shown) for removing an excessive ink adhering to the head is placed, and then be subjected to wiping or the like for cleaning. A conventional method can be directly used for a specific method for cleaning.

After the completion of the image drawing, the recording medium on which an image has been drawn is replaced with a new recording medium by using a transferring mechanism for a recording medium (not shown).

The above embodiment of the present invention can be modified or changed without departing from the gist of the present invention. For example, the above description has shown the case where the head 70 is moved in the X and Y directions. However, it is also possible that the head 70 be moved only in the X direction (or the Y direction) whereas the recording medium be moved in the Y direction (or the X direction), to perform image drawing while the movements are made to be in synchronization with each other.

The present invention includes means (such as an electrothermal converter or laser beam) for generating heat energy as energy used for performing ejection of an ink-jet ink, and the head that ejects the ink-jet ink by virtue of the heat energy exhibits an excellent effect. According to such a method, a drawn image can have an increased definition. The use of the ink composition for ink jet of the present invention enables more excellent image drawing to be performed.

The typical structure or principle of an apparatus including the means for generating heat energy preferably employs a basic principle disclosed in, for example, U.S. Pat. No. 4,723, 129 or U.S. Pat. No. 4,740,796. The principle can be applied to both of so-called on-demand type and continuous type but is particularly effective in the case of the on-demand type. The reason for this is as follows. At least one driving signal, which corresponds to ejection information and provides a rapid temperature increase exceeding nuclear boiling, is applied to an electrothermal converter that holds a liquid and is placed in correspondence with a flow path. Thus, the electrothermal converter is allowed to generate heat energy and film boiling is caused on a heat acting surface of the head. As a result, an air bubble can be formed in the liquid in one-to-one correspondence with the driving signal. The growth and shrinkage of the air bubble allow the liquid to be ejected from an opening for ejection, thereby resulting in the formation of at least one droplet. The driving signal is more preferably of a pulse shape because the growth and shrinkage of an air bubble can be performed appropriately and in an instant so that ejection of a liquid particularly excellent in response can be achieved. A driving signal disclosed in U.S. Pat. No. 4,463,359 or U.S. Pat. No. 4,345,262 is appropriate for the pulse-shape driving signal. The employment of conditions described in U.S. Pat. No. 4,313,124 of the invention concerning a temperature increase rate on the heat acting surface enables more excellent ejection to be performed.

With regard to the structure of the head, the present invention also includes structures applying U.S. Pat. No. 4,558,333 and U.S. Pat. No. 4,459,600 each disclosing a structure in which a heat acting portion is arranged in a curving region in addition to a combined structure of an ejection port, a liquid path, and an electrothermal converter (a linear liquid flow path or a right-angled liquid flow path). In addition, the effects of the present invention are effective in a structure based on Japanese Patent Application Laid-Open No. S59-123670 disclosing a structure in which a common slit among a plurality of electrothermal converters is provided as an ejection portion of the electrothermal converters or in a structure based on Japanese Patent Application Laid-Open No. S59-138461 disclosing a structure in which an opening for absorbing a pressure wave of heat energy corresponds to an ejection portion. That is, according to the present invention, the ejection of an ink-jet ink can be efficiently performed with reliability regardless of the shape of a head.

The present invention can also be effectively applied to a full-line type head having a length corresponding to the maximum width of a recording medium in the image forming apparatus of the present invention. Such a head may have a structure in which a plurality of heads are combined to satisfy the length or a structure as an integrally formed one head.

In addition, the present invention is effective in the case where a head fixed to an apparatus main body or an exchangeable chip type head, which is mounted on an apparatus main body to enable electrical connection with the apparatus main body or ink supply from the apparatus main body, is used even if the head is of a serial type.

The apparatus of the present invention may further include liquid droplet removing means. Provision of such means enables a more excellent ejection effect to be realized.

Addition of preliminary auxiliary means or the like to the structure of the apparatus of the present invention is preferable because the effects of the present invention can be further stabilized. Specific examples of such means include: capping means for a head; pressurizing or sucking means; an electrothermal converter or another heating element; preheating means that performs heating by using a combination of them; and pre-ejection means for performing ejection different from ink ejection.

Performing the film boiling method described above is most effective for the present invention.

In the apparatus of the present invention, the amount of ink ejected from each ejection port of an ejection head of an ink-jet ink is preferably in the range of 0.1 pl to 100 pl.

The ink composition of the present invention can also be used for an indirect recording apparatus using a recording method including: printing an ink onto an intermediate transfer member; and transferring the printed ink onto a recording medium such as paper. The ink composition of the present invention can also be applied to a direct recording apparatus using an intermediate transfer member.

Hereinafter, the present invention will be described in more detail by way of examples. However, the present invention is not limited to these examples.

EXAMPLE 1

<Synthesis of $CH_2=CHOCH_2CH_2OPh(COOCH_3)_2$>

0.42 mol of 2-chloroethyl vinyl ether was added to 0.8 mol of potassium carbonate, 0.42 mol of dimethyl-5-hydroxy-isophthalate, and 4 g of tetrabutylammonium iodide in 300 ml of ethanol under a nitrogen atmosphere, and the whole was refluxed under heating under a nitrogen atmosphere for 40 hours. After the completion of the reaction, the resultant was diluted with water and left to stand overnight. After that, the reaction solution was filtered, the solvent was distilled off, and the resultant was subjected to column chromatography. After that, recrystallization with a mixed solvent of methanol/toluene/hexane was repeated, the solvent was distilled off, and the resultant was dried to obtain a polymerizable compound $CH_2=CHOCH_2CH_2OPh(COOCH_3)_2$.

EXAMPLE 2

<Synthesis of Polymer Compound>

0.1 mol of the polymerizable compound obtained in Example 1, 0.001 mol of water, and 0.005 mol of ethyl aluminum dichloride were subjected to cationic polymerization in anhydrous toluene.

20 hours after that, the reaction was terminated. Then, methylene chloride and water were added to the resultant. Then, the whole was washed with water, dilute hydrochloric acid, and an alkali, and was then dried with anhydrous sodium sulfate, and the solvent was distilled off, thereby resulting in a polymer compound (polymer). The polymer compound had a number average molecular weight of 3,600 according to size-exclusion chromatography.

EXAMPLE 3

<Synthesis of $CH_2=CHO(CH_2CH_2O)_2Ph(COOCH_3)_2$>

Synthesis was performed in the same manner as that described above except that 2-chloroethyl vinyl ether in Example 1 was changed to $CH_2=CHO(CH_2CH_2O)_2OTs$ (Ts represents a tosyl group) to obtain a target polymerizable compound $CH_2=CHO(CH_2CH_2O)_2Ph(COOCH_3)_2$.

EXAMPLE 4

<Synthesis of Polymer Compound 2>

The polymerizable compound obtained in Example 3 was polymerized in the same manner as in Example 2 to obtain a polymer compound. The polymer compound had a number average molecular weight of 2,100 according to size-exclusion chromatography.

EXAMPLE 5

The polymer compound (polymer) synthesized in Example 2 was stirred with a 5N aqueous solution of sodium hydroxide for 40 hours at room temperature (23° C.) to hydrolyze an ester. The resultant was neutralized with 5N hydrochloric acid, extracted with methylene chloride, and dried, and then the solvent was distilled off, thereby resulting in a free carboxylic acid polymer. The polymer was neutralized with an equivalent amount of 1N sodium hydroxide, and water was distilled off, thereby resulting in a sodium carboxylate polymer.

EXAMPLE 6

2 parts by mass of a pigment (trade name: MOGUL-L; available from Cabot Corporation), 3 parts by mass of the sodium carboxylate-type polymer compound of Example 5, and 25 parts by mass of diethylene glycol were added to and dispersed into 177 parts by mass of ion-exchanged water by using an ultrasonic homogenizer. The dispersion was filtered through a 1-μm filter under pressure to prepare an ink composition. The dispersibility of the pigment was good.

EXAMPLE 7

Ink jet recording was performed by using the ink composition prepared in Example 6. The ink composition of Example 6 was charged into an ink tank of a bubble jet (registered trademark) printer (trade name: BJJ-800J; manufactured by Canon Inc.), and then recording was performed on plain paper by using the ink jet printer. As a result, fine black letters were printed.

EXAMPLE 8

A toner composition was produced as described below by using a free carboxylic acid polymer serving as a precursor for the sodium carboxylate polymer obtained in Example 5.

10 parts by mass of a polyester resin (synthesized by using bisphenol A, terephthalic acid, n-dodecenylsuccinic acid, trimellitic acid, and diethylene glycol at a molar ratio of 20:38:10:5:27), 70 parts by mass of magnetite ($Fe_3O_4$), 3 parts by mass of the free carboxylic acid polymer described above, 2 parts by mass of a triphenylmethane-based dye, and 3 parts by mass of low-molecular-weight polypropylene were premixed, and the mixture was melted and kneaded by using an extruder. The resultant was cooled, coarsely pulverized with a speed mill, finely pulverized with a jet mill, and classified with a zigzag classifier to obtain a toner having a volume average particle size of 11 μm.

0.4 part by mass of positively-charged hydrophobic dry silica, which had been treated with amino-modified silicone oil (having a viscosity of 100 cp at 25° C. and an amine equivalent of 800), and 0.2 part by mass of spherical PVDF particles having an average particle size of 0.2 μm were added to 100 parts by mass of the toner, and the whole was mixed by using a Henschel mixer to obtain a positively-charged toner composition. Printing was performed by using the toner composition and a copying machine NP-3525 manufactured by Canon Inc., with the result that fine letters were printed.

EXAMPLE 9

<Synthesis of Diblock Polymer 1>

Synthesis of a diblock polymer composed of a block segment (A block) of a random copolymer of isobutyl vinyl ether (IBVE) and biphenyl oxyethyl vinyl ether (VEEtPhPh), and a block segment (B block) of a polymer of 1,3-dimethylphthalic acid 5-oxyethyl vinyl ether ($VEEtPh(COOMe)_2$)

The air inside a glass vessel equipped with a three-way cock was replaced with nitrogen, and the system was heated to 250° C. under a nitrogen gas atmosphere to remove adsorbed water. After the system had been returned to room temperature, 2.5 mmol of IBVE, 2.5 mmol of VEEtPhPh, 16 mmol of ethyl acetate, 0.05 mmol of 1-isobutoxyethyl acetate, and 11 ml of toluene were added, and the reaction system was cooled. When the temperature inside the system reached 0° C., 0.2 mmol of ethyl aluminum sesquichloride (equimolar mixture of diethyl aluminum chloride and ethyl aluminum dichloride) was added to start polymerization. The molecular weight was monitored periodically by means of gel permeation chromatography (GPC) to confirm the completion of the polymerization of the A block. The polymerization was judged to be complete when the molecular weight reached a predetermined molecular weight in monitoring by means of GPC (the same holds true for the following). At this stage, Mn=9,700 and Mw/Mn=1.18.

Next, a solution of 10 mmol of $VEEtPh(COOMe)_2$ serving as a monomer of the B block in toluene was added to continue the polymerization. 24 hours after that, the polymerization reaction was stopped (rate of polymerization of VEEtPh $(COOMe)_2$: 40%). The polymerization reaction was stopped by adding a 0.3-mass % aqueous solution of ammonia/methanol to the system. The reaction mixture solution was diluted with dichloromethane, and the diluted product was washed with 0.6M hydrochloric acid 3 times and with distilled water 3 times. The resultant organic phase was concentrated and dried by using an evaporator and dried in a vacuum, and the resultant was repeatedly subjected to dialysis in a methanol solvent by using a semipermeable membrane of cellulose to remove a monomer compound. As a result, a diblock polymer as a target product was obtained. The diblock polymer was identified by means of NMR and GPC. The diblock copolymer had Mn=16,300 and Mw/Mn=1.18. The polymerization degree ratio between the respective blocks (monomer unit ratio) was A:B=100:40. The polymerization degree ratio between the two types of monomers in the A block was 1:1. The glass transition point (Tg) of the polymer was measured by means of DSC, with the result that the glass transition point was observed at 7° C.

Furthermore, the resultant polymer compound (polymer) was hydrolyzed in the same manner as in Example 5 to obtain a free carboxylic acid polymer. In addition, the polymer was neutralized with an equivalent amount of 1N sodium hydroxide, and water was distilled off to obtain a sodium carboxylate polymer.

EXAMPLE 10

An ink composition was prepared in the same manner as in Example 6 by using the sodium carboxylate-type polymer compound of Example 9. The dispersibility of the pigment was good.

EXAMPLE 11

Ink jet recording was performed in the same manner as in Example 7 by using the ink composition prepared in Example 10, with the result that fine black letters were printed. An optical density (O.D.) of the resultant image was evaluated by measuring the optical density (O.D.) of the image with a reflection densitometer (trade name: RD-19A; manufactured by Sakata Inx Corporation). The optical density measured was 0.98.

COMPARATIVE EXAMPLE 1

An ink composition was prepared in the same manner as that for the ink composition prepared in Example 10 by using a sodium carboxylate of a styrene-acrylic acid diblock copolymer (Mn=13,600, Mw/Mn=1.32, styrene/acrylic acid=50/50 (monomer unit ratio)) as a polymer. A letter image was recorded on plain paper by using the ink composition and the ink jet printer. As a result, the image faded. In addition, the image was evaluated for optical density (O.D.) in the same manner as in Example 11, with the result that the optical density (O.D.) of the image was 0.46.

COMPARATIVE EXAMPLE 2

A letter image was recorded on plain paper in the same manner as in Example 11 by using the ink composition prepared in Example 10. 1 minute after the printing, a line marker test was performed, with the result that a printed product showed no smears at an image trailing edge. Meanwhile, the ink composition prepared in Comparative Example 1 and containing a sodium carboxylate of a styrene-acrylic acid diblock copolymer as a polymer was similarly printed on plain paper. 1 minute after the printing, a line marker test was performed, with the result that a black smear at an image trailing edge was clearly observed.

EXAMPLE 12

<Synthesis of Diblock Copolymer 2>

A diblock polymer, poly[EOVE-b-VEEtPh(COOMe)$_2$] was synthesized by using 5.0 mmol of 2-ethoxyethyl vinyl ether (EOVE) exhibiting hydrophilicity at a temperature of 20° C. or lower and hydrophobicity at a temperature higher than 20° C. (upper limit temperature of hydration) instead of 2.5 mmol of IBVE and 2.5 mmol of VEEtPhPh serving as monomers of the A component in Example 9. The synthesized compound was identified by means of GPC and NMR in the same manner as that described above. The compound had Mn=21,600 and Mw/Mn=1.22. The polymerization degree ratio between the respective blocks was A:B=100:40. The other synthesis conditions were identical to those of Example 9.

Next, an ester portion was hydrolyzed in the same manner as in Example 5 to obtain a free carboxylic acid polymer and a sodium carboxylate polymer.

In addition, 10 parts by mass of the resultant sodium carboxylate-type diblock polymer and 5 parts by mass of an oil-soluble dye Oil Blue N (trade name, available from Sigma Aldrich) were co-dissolved into dimethylformamide, and the whole was turned into an aqueous phase by using 400 parts by mass of distilled water to obtain an ink composition. The ink composition was left to stand for 10 days, but the Oil Blue was neither separated nor precipitated.

In addition, the dye-dispersed composition was cooled to 10° C., the polymer micelle was broken, and the polymer was dissolved into water. As a result, the dye and the dye solution were separated from each other, and the aqueous phase became colorless. The result confirmed that a colorant was included in the polymer micelle.

EXAMPLE 13

Toner compositions were produced in the same manner as in Example 8 by using free carboxylic acid polymers serving as precursors for the sodium carboxylate polymers obtained in Examples 5 and 9, thereby resulting in toners each having a volume average particle size of 11 μm.

Each of the toners was treated in the same manner as in Example 8 to obtain a positively-charged toner composition. Printing was performed by using each of the toner compositions and a copying machine (trade name: NP-3525; manufactured by Canon Inc.), with the result that fine letters were printed in each case.

EXAMPLE 14

<Synthesis of Triblock Polymer 1>

Synthesis of a triblock polymer composed of a block segment (A block) of a random copolymer of isobutyl vinyl ether (IBVE) and biphenyl oxyethyl vinyl ether (VEEtPhPh), a block segment (B block) of a polymer of 2-methoxyethyl vinyl ether (MOVE), and a block segment (C block) of a polymer of 1,3-dimethylphthalic acid 5-oxyethyl vinyl ether (VEEtPh (COOMe)$_2$)

The air inside a glass vessel equipped with a three-way cock was replaced with nitrogen, and the system was heated to 250° C. under a nitrogen gas atmosphere to remove adsorbed water. After the system had been returned to room temperature, 2.5 mmol of IBVE, 2.5 mmol of VEEtPhPh, 16 mmol of ethyl acetate, 0.05 mmol of 1-isobutoxyethyl acetate, and 11 ml of toluene were added, and the reaction system was cooled. When the temperature inside the system reached 0° C., 0.2 mmol of ethyl aluminum sesquichloride (equimolar mixture of diethyl aluminum chloride and ethyl aluminum dichloride) was added to start polymerization. The molecular weight was monitored periodically by means of gel permeation chromatography (GPC) to confirm the completion of the polymerization of the A block. At this stage, Mn=9,500 and Mw/Mn=1.16.

Next, 10 mmol of MOVE serving as a monomer of the B block was added to continue the polymerization. After the completion of the polymerization of the B block had been confirmed through monitoring by means of GPC (Mn=34,200 and Mw/Mn=1.17 at this stage), 10 mmol of VEEtPh (COOMe)$_2$ serving as a monomer of the C block was added to continue the polymerization. 24 hours after that, the polymerization reaction was stopped (rate of polymerization of VEEtPh(COOMe)$_2$: 26%). The polymerization reaction was stopped by adding a 0.3-mass % aqueous solution of ammonia/methanol to the system. The reaction mixture solution was diluted with dichloromethane, and the diluted product was washed with 0.6M hydrochloric acid 3 times and with distilled water 3 times. The resultant organic phase was concentrated and dried by using an evaporator and dried in a vacuum, and a triblock polymer as a target product was isolated from the resultant. The triblock polymer was identified by means of NMR and GPC. The triblock polymer had Mn=39,400 and Mw/Mn=1.14. The polymerization degree ratio was A:B:C=100:200:26. The polymerization degree ratio between the two types of monomers in the A block was 1:1.

EXAMPLE 15

<Synthesis of Triblock Polymer 2>

Synthesis of a triblock polymer composed of a block segment (A block) of a polymer of 4-methylbenzene oxyethyl vinyl ether (TolOVE), a block segment (B block) of a polymer of 2-methoxyethyl vinyl ether (MOVE), and a block segment (C block) of a polymer of 1,3-dimethylphthalic acid 5-oxyethyl vinyl ether (VEEtPh(COOMe)$_2$)

First, the A block was polymerized in the same manner as in Example 14 except that 5.0 mmol of TolOVE were added as a monomer of the A block instead of IBVE and VEEtPhPh in Example 14. The molecular weight was monitored periodically by means of gel permeation chromatography (GPC) to confirm the completion of the polymerization of the A block. At this stage, Mn=12,000 and Mw/Mn=1.18.

After that, the B block and then the C block were polymerized under the same conditions as those of Example 14. At the time of the completion of the polymerization of the B block, Mn=37,800 and Mw/Mn=1.20 in monitoring by means of GPC. The polymerization reaction of the C block was stopped when the rate of polymerization of VEEtPh(COOMe)$_2$ reached 25%. A treatment after the polymerization was performed in the same manner as in Example 14. The resultant organic phase was concentrated and dried by using an evaporator and dried in a vacuum, and a triblock polymer as a target product was isolated from the resultant. The triblock polymer was identified by means of NMR and GPC. The triblock had Mn=41,500 and Mw/Mn=1.16. The polymerization degree ratio was A:B:C=100:200:24.

EXAMPLE 16

The polymer compound (polymer) synthesized in Example 14 was hydrolyzed in the same manner as in Example 5 to obtain a free carboxylic acid polymer. In addition, the polymer was neutralized with an equivalent amount of 1N sodium hydroxide, and water was distilled off to obtain a sodium carboxylate polymer.

EXAMPLE 17

The polymer compound synthesized in Example 15 was hydrolyzed and extracted in the same manner as in Example 5 to obtain a free carboxylic acid polymer and a sodium carboxylate polymer.

EXAMPLE 18

An ink composition was prepared in the same manner as in Example 6 by using 2 parts by mass of a pigment (trade name: MOGUL-L; available from Cabot Corporation) and 3 parts by mass of the sodium carboxylate-type polymer compound of Example 16. The dispersibility of the pigment was good.

EXAMPLE 19

An ink composition was prepared in the same manner as in Example 18 by using the sodium carboxylate-type polymer compound of Example 17. The dispersibility of the pigment was good.

EXAMPLE 20

Ink jet recording was performed in the same manner as in Example 7 by using each of the ink compositions prepared in Example 18 and Example 19. A letter image was recorded on plain. paper, with the result that fine black letters were printed in each case.

EXAMPLE 21

<Synthesis of Triblock Polymer 3>

A triblock polymer, poly[EOVE-b-MOVE-b-VEEtPh (COOMe)$_2$] was synthesized by using 5.0 mmol of 2-ethoxyethyl vinyl ether (EOVE) exhibiting hydrophilicity at a temperature of 20° C. or lower and hydrophobicity at a temperature higher than 20° C. (upper limit temperature of hydration) instead of 5.0 mmol of TolOVE as a monomer of the A component in Example 15. The synthesized compound was identified by means of GPC and NMR in the same manner as that described above. The compound had Mn=43,100 and Mw/Mn=1.25. The polymerization degree ratio among the respective blocks was A:B:C=100:200:25. The other synthesis conditions were identical to those of Example 15.

In addition, 10 parts by mass of the resultant triblock polymer and 5 parts by mass of an oil-soluble dye Oil Blue N (trade name, available from Sigma Aldrich) were co-dissolved into dimethylformamide, and the whole was turned into an aqueous phase by using 400 parts by mass of distilled water to obtain an ink composition. The ink composition was left to stand for 10 days, but the Oil Blue was neither separated nor precipitated.

In addition, the dye-dispersed composition was cooled to 10° C., the polymer micelle was broken, and the polymer was dissolved into water. As a result, the dye and the dye solution were separated from each other, and the aqueous phase became colorless. The result confirmed that a colorant was included in the polymer micelle.

COMPARATIVE EXAMPLE 3

The ink composition prepared in Example 18 and an ink composition prepared in the same manner as in Example 18 by using a sodium carboxylate of an acrylic acid-styrene-acrylic acid triblock copolymer (Mn=18,500, Mw/Mn=1.33, acrylic acid/styrene/acrylic acid=50/60/50 (monomer unit ratio)) as a polymer were used to record letter images on plain paper by using the ink jet printer, and the images were evaluated for optical density (O.D.). The optical density (O.D.) of each of the resultant images was measured with a reflection densitometer (manufactured by Sakata Inx Corporation, RD-19A). As a result, the optical density was 1.05 for the ink composition of Example 18 whereas the optical density was 0.58 for the ink composition using the acrylic acid-styrene-acrylic acid triblock copolymer. Comparison between the ink compositions shows that the latter ink composition had poor dispersibility. Therefore, the latter ink composition had poor ejectability and provided a printed image with a low optical density (O.D.).

COMPARATIVE EXAMPLE 4

Letter images were recorded on plain paper in the same manner as in Example 20 by using the ink compositions prepared in Example 18 and Example 19. 1 minute after the printing, a line marker test was performed, with the result that printed products of Example 18 and Example 19 showed no smears at image trailing edges. Meanwhile, the ink composition prepared in Comparative Example 3 and containing a sodium carboxylate of an acrylic acid-styrene-acrylic acid triblock copolymer as a polymer was similarly printed on plain paper. 1 minute after the printing, a line marker test was performed, with the result that a black smear at an image trailing edge was clearly observed.

EXAMPLE 22

Toner compositions were produced in the same manner as in Example 8 by using free carboxylic acid polymers serving as precursors for the sodium carboxylate polymers obtained in Example 18 and Example 19, thereby resulting in toners each having a volume average particle size of 11 μm.

Each of the toners was treated in the same manner as in Example 8 to obtain a positively-charged toner composition. Printing was performed by using each of the toner compositions and a copying machine (trade name: NP-3525; manufactured by Canon Inc.), with the result that fine letters were printed in each case.

EXAMPLE 23

<Synthesis of Triblock Polymer 4>

Synthesis of a triblock polymer composed of a block segment (A block) of a polymer of 2-methoxyethyl vinyl ether (MOVE), a block segment (B block) of a random copolymer of isobutyl vinyl ether (IBVE) and biphenyl oxyethyl vinyl ether (VEEtPhPh), and a block segment (C block) of a polymer of 1,3-dimethylphthalic acid 5-oxyethyl vinyl ether (VEEtPh(COOMe)$_2$) First, the A block was polymerized in the same manner as in Example 14 by using 10 mmol of MOVE as a monomer of the A block. The completion of the polymerization of the A block was confirmed through monitoring by means of GPC. At this stage, Mn=92,500 and Mw/Mn=1.19.

Next, a solution of 2.5 mmol of IBVE and 2.5 mmol of VEEtPhPh serving as monomers of the B block in toluene was added to continue the polymerization. After the completion of the polymerization of the B block had been confirmed through monitoring by means of GPC (Mn=34,800 and Mw/Mn=1.22 at this stage), a solution of 10 mmol of VEEtPh (COOMe)$_2$ serving as a monomer of the C block in toluene was added to continue the polymerization. 24 hours after that, the polymerization reaction was stopped (rate of polymerization of VEEtPh(COOMe)$_2$:26%). A treatment after the polymerization and drying were performed in the same manner as in Example 14 to isolate a triblock polymer as a target product. The triblock polymer had Mn=38,400 and Mw/Mn=1.18. The polymerization degree ratio was A:B:C=200:100:26. The polymerization degree ratio between two types of monomers in the B block was 1:1.

EXAMPLE 24

The polymer compound (polymer) synthesized in Example 23 was hydrolyzed in the same manner as in Example 5 to obtain a free carboxylic acid polymer. In addition, the polymer was neutralized with an equivalent amount of 1N sodium hydroxide, and water was distilled off to obtain a sodium carboxylate polymer.

EXAMPLE 25

An ink composition was prepared in the same manner as in Example 6 by using 2 parts by mass of a pigment (trade name: MOGUL-L; available from Cabot Corporation) and 3 parts by mass of the sodium carboxylate-type polymer compound of Example 24. The dispersibility of the pigment was good.

EXAMPLE 26

Ink jet recording was performed in the same manner as in Example 7 by using the ink composition prepared in Example 25. A letter image was recorded on plain paper, with the result that fine black letters were printed. 1 minute after the printing, the printed portion was strongly rubbed with a line marker 3 times, but no black smears at an image trailing edge was observed so that fixing property was found to be excellent. In addition, water was dropped onto the printed portion, but no bleeding was observed so that water resistance was found to be excellent. The optical density (O.D.) of the resultant image was measured with a reflection densitometer (trade name: RD-19A; manufactured by Sakata Inx Corporation). The optical density measured was 0.97.

EXAMPLE 27

<Synthesis of Triblock Polymer 5>

A triblock polymer, poly[MOVE-b-EOVE-b-VEEtPh (COOMe)$_2$] was synthesized by using 5.0 mmol of 2-ethoxyethyl vinyl ether (EOVE) exhibiting hydrophilicity at a temperature of 20° C. or lower and hydrophobicity at a temperature higher than 20° C. (upper limit temperature of hydration) instead of 2.5 mmol of IBVE and 2.5 mmol of VEEtPhPh as monomers of the B component in Example 2-3. The synthesized compound was identified by means of GPC and NMR in the same manner as that described above. The compound had Mn=31,600 and Mw/Mn=1.31. The other synthesis conditions were identical to those of Example 24.

In addition, 10 parts by mass of the resultant triblock polymer and 5 parts by mass of an oil-soluble dye Oil Blue N (trade name, available from Sigma Aldrich) were co-dissolved into dimethylformamide, and the whole was turned into an aqueous phase by using 400 parts by mass of distilled water to obtain an ink composition. The ink composition was left to stand for 10 days, but the Oil Blue was neither separated nor precipitated.

In addition, the dye-dispersed composition was cooled to 10° C., a polymer micelle was broken, and the polymer was dissolved into water. As a result, the dye and the dye solution were separated from each other, and the aqueous phase became colorless. The result confirmed that a colorant was included in the polymer micelle.

COMPARATIVE EXAMPLE 5

An ink composition was prepared in the same manner as in Example 25 by using a sodium carboxylate of an acrylic acid-styrene-acrylic acid triblock copolymer (Mn=18,500, Mw/Mn=1.33, acrylic acid/styrene/acrylic acid=50/60/50 (monomer unit ratio)) as a polymer. A letter image was recorded on plain paper by using the ink composition and the ink jet printer, with the result that the letter image was observed to fade (a non-printed portion was observed). In addition, the image was evaluated for optical density (O.D.) in the same manner as in Example 26. As a result, the optical density (O.D.) of the resultant image was 0.58.

COMPARATIVE EXAMPLE 6

The ink composition prepared in Comparative Example 5 and containing a sodium carboxylate of an acrylic acid-styrene-acrylic acid triblock copolymer as a polymer was printed on plain paper in the same manner as in Example 26. 1 minute after the printing, a line marker test was performed, with the result that a black smear at an image trailing edge was clearly observed.

EXAMPLE 28

A toner composition was produced in the same manner as in Example 8 by using a free carboxylic acid polymer serving as a precursor for the sodium carboxylate polymer obtained in Example 2 4, thereby resulting in a toner having a volume average particle size of 11 μm.

The toner was treated in the same manner as in Example 8 to obtain a positively-charged toner composition. Printing was performed by using the toner composition and a copying machine (trade name:NP-3525; manufactured by Canon Inc.), with the result that fine letters were printed.

EXAMPLE 29

<Synthesis of Polymer Compound 3>
Synthesis of a polymer compound composed of a copolymer of 4-{(vinyloxy)ethoxy}ethyl benzoate (VEEtPh-COOEt) and 1,3-dimethylphthalic acid 5-oxyethyl vinyl ether (VEEtPh(COOMe)$_2$)

The air inside a glass vessel equipped with a three-way cock was replaced with nitrogen, and the system was heated to 250° C. under a nitrogen gas atmosphere to remove adsorbed water. After the system had been returned to room temperature, 10 mmol of VEEtPhCOOEt, 10 mmol of VEEtPh(COOMe)$_2$, 16 mmol of ethyl acetate, 0.05 mmol of 1-isobutoxyethyl acetate, and 11 ml of toluene were added, and the reaction system was cooled. When the temperature inside the system reached 0° C., 0.2 mmol of ethyl aluminum sesquichloride (equimolar mixture of diethyl aluminum chloride and ethyl aluminum dichloride) was added to start polymerization. 24 hours after that, the polymerization reaction was stopped. The polymerization reaction was stopped by adding a 0.3-mass % aqueous solution of ammonia/methanol to the system., The reaction mixture solution was diluted with dichloromethane, and the diluted product was washed with 0.6M hydrochloric acid 3 times and with distilled water 3 times. The resultant organic phase was concentrated and dried by using an evaporator and dried in a vacuum, and a polymer as a target product was isolated from the resultant. The polymer was identified by means of NMR and gel permeation chromatography (GPC). The polymer had Mn=13,500 and Mw/Mn=1.22. The polymerization degree ratio between two types of monomers was 5:5.

<Synthesis of Polymer Compound 4>
Synthesis of a polymer compound composed of a copolymer of 4-{(vinyloxy)ethoxy}ethyl benzoate (VEEtPh-COOEt) and 1,3-dimethylphthalic acid 5-oxyethyl vinyl ether (VEEtPh(COOMe)$_2$)

Polymerization was performed in the same manner as in Example 29. 8 hours after that, the polymerization reaction was stopped. A treatment after the polymerization was performed in the same manner as in Example 29. The polymer was identified by means of NMR and gel permeation chromatography (GPC). The polymer had Mn=5,400 and Mw/Mn=1.27. The polymerization degree ratio between the two types of monomers (VEEtPhCOOEt and VEEtPh(COOMe)$_2$) was 6:4.

EXAMPLE 31

<Synthesis of Diblock Polymer 3>
Synthesis of a diblock polymer composed of a block segment (A block) of a polymer of 4-methylbenzene oxyethyl vinyl ether (TolOVE) and a block segment (B block) of a copolymer of 4-{(vinyloxy)ethoxy}ethyl benzoate (VEEtPh-COOEt) and 1,3-dimethylphthalic acid 5-oxyethyl vinyl ether (VEEtPh (COOMe)$_2$)

First, the A block was polymerized in the same manner as in Example 29 except that 5.0 mmol of TolOVE were added as a monomer of the A block. The molecular weight was monitored periodically by means of gel permeation chromatography (GPC) to confirm the completion of the polymerization of the A block. At this stage, Mn=12,000 and Mw/Mn=1.18.

After that, 10 mmol of each of the monomers (VEEtPh-COOEt and VEEtPh(COOMe)$_2$) of the B block were added to continue the polymerization. 24 hours after that, the polymerization reaction was stopped. A treatment after the polymerization was performed in the same manner as in Example 29. The resultant organic phase was concentrated and dried by using an evaporator and dried in a vacuum, and a diblock polymer as a target product was isolated from the resultant. The diblock polymer was identified by means of NMR and GPC. The diblock polymer had Mn=26,900 and Mw/Mn=1.21. The polymerization degree ratio was A:B=100:70. The polymerization degree ratio between the two types of monomers in the B block was 5:5.

EXAMPLE 32

The polymer compound (polymer) synthesized in Example 29 was hydrolyzed in the same manner as in Example 5 to obtain a free carboxylic acid polymer. In addition, the polymer was neutralized with an equivalent amount of 1N sodium hydroxide, and water was distilled off to obtain a sodium carboxylate polymer.

EXAMPLE 33

The polymer compound synthesized in Example 30 was hydrolyzed and extracted in the same manner as in Example 32 to obtain a free carboxylic acid polymer and a sodium carboxylate polymer.

EXAMPLE 34

The polymer compound synthesized in Example 31 was hydrolyzed and extracted in the same manner as in Example 32 to obtain a free carboxylic acid polymer and a sodium carboxylate polymer.

EXAMPLE 35

An ink composition was prepared in the same manner as in Example 6 by using 2 parts by mass of a pigment (trade name: MOGUL-L; available from Cabot Corporation) and 3 parts by mass of the sodium carboxylate-type polymer compound of Example 34. The dispersibility of the pigment was good.

EXAMPLE 36

Ink jet recording was performed in the same manner as in Example 7 by using the ink composition prepared in Example 35. A letter image was recorded on plain paper, with the result that fine black letters were printed. In addition, the optical density (O.D.) of the resultant image was evaluated by measuring the optical density (O.D.) of the image with a reflection densitometer (trade name: RD-19A; manufactured by Sakata Inx Corporation). The optical density measured was 0.94.

EXAMPLE 37

<Synthesis of Diblock Polymer 4>

A diblock polymer, poly[EOVE-b-(VEEtPhCOOEt-r-VEEtPh(COOMe)$_2$)] was synthesized by using 5.0 mmol of 2-ethoxyethyl vinyl ether (EOVE) exhibiting hydrophilicity at a temperature of 20° C. or lower and hydrophobicity at a temperature higher than 20° C. (upper limit temperature of hydration) instead of 5.0 mmol of TolOVE as a monomer of the A component in Example 31. The synthesized compound was identified by means of GPC and NMR in the same manner as that described above. The compound had Mn=21,600 and Mw/Mn=1.32. The other synthesis conditions were identical to those of Example 31.

In addition, 10 parts by mass of the resultant diblock polymer and 5 parts by mass of an oil-soluble dye Oil Blue N (trade name, available from Sigma Aldrich) were co-dissolved into dimethylformamide, and the whole was turned into an aqueous phase by using 400 parts by mass of distilled water to obtain an ink composition. The ink composition was left to stand for 10 days, but the Oil Blue was neither separated nor precipitated.

In addition, the dye-dispersed composition was cooled to 10° C., the polymer micelle was broken, and the polymer was dissolved into water. As a result, the dye and the dye solution were separated from each other, and the aqueous phase became colorless. The result confirmed that a colorant was included in the polymer micelle.

COMPARATIVE EXAMPLE 7

An ink composition was prepared in the same manner as that for the ink composition prepared in Example 35 by using a sodium carboxylate of a styrene-acrylic acid diblock copolymer (Mn=13,600, Mw/Mn=1.32, styrene/acrylic acid=50/50 (monomer unit ratio)) as a polymer. A letter image was recorded on plain paper by using the ink composition and the ink jet printer, with the result that the letter image faded. In addition, the image was evaluated for optical density (O.D.) in the same manner as in Example 36. As a result, the optical density (O.D.) of the image was 0.56.

COMPARATIVE EXAMPLE 8

4 parts by mass of each of the sodium carboxylate polymer obtained in Example 33 and a sodium salt polymer obtained by neutralizing polymaleic acid (Mn=3,000, Mw/Mn=1.36) with an equivalent amount of sodium hydroxide, 2 parts by mass of a pigment (trade name: MOGUL-L; available from Cabot Corporation), and 25 parts by mass of diethylene glycol were added to and dispersed into 177 parts by mass of ion-exchanged water by using an ultrasonic homogenizer. Each of the dispersions was filtered through a 1-μm filter under pressure to prepare an ink composition. After that, an aqueous solution of sodium hydroxide was added to each of the ink compositions in such a manner that the pH of the solutions was adjusted to 8.3 and 12.0. Those solutions were immersed in a thermostatic bath at 80° C. and left to stand for 10 days. As a result, the aqueous solution of Example 33 showed no change at pH's of 8.3 and 12.0. The aqueous solution of polymaleic acid showed no change at a pH of 12.0, but a gel-like suspended matter and a precipitate were observed in the ink composition at a pH of 8.3.

COMPARATIVE EXAMPLE 9

A letter image was recorded on plain paper in the same manner as in Example 36 by using the ink composition prepared in Example 35. 1 minute after the printing, a line marker test was performed, with the result that a printed product obtained by using Example 35 showed no smears at an image trailing edge. Meanwhile, the ink composition prepared in Comparative Example 7 and containing a sodium carboxylate of a styrene-acrylic acid diblock copolymer as a polymer was similarly printed on plain paper. 1 minute after the printing, a line marker test was performed, with the result that a black smear at an image trailing edge was clearly observed.

EXAMPLE 38

A toner composition was produced in the same manner as in Example 8 by using a free carboxylic acid polymer serving as a precursor for the sodium carboxylate polymer obtained in Example 34, thereby resulting in a toner having a volume average particle size of 11 μm.

The toner was treated in the same manner as in Example 8 to obtain a positively-charged toner composition. Printing was performed by using the toner composition and a copying machine (trade name: NP-3525; manufactured by Canon Inc.), with the result that fine letters were printed.

This application claims priority from Japanese Patent Application Nos. 2003-372462 filed on Oct. 31, 2003, 2003-434553 filed on Dec. 26, 2003 and 2004-139053 filed on May 7, 2004, which are hereby incorporated by reference herein.

What is claimed is:

1. A polymer compound having a repeating unit structure represented by the following general formula (2):

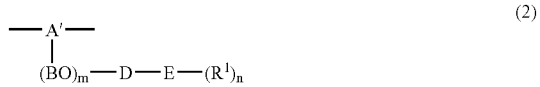

wherein A' represents a polyalkenyl ether group which may be substituted; B represents a linear or branched alkylene group having 1 to 15 carbon atoms which may be substituted; m represents an integer from 0 to 30; when m is larger than 1, B may be different from each other; D represents a single bond or a linear or branched alkylene group having 1 to 10 carbon atoms which may be substituted; E represents any one of an aromatic ring which may be substituted, a condensed ring which may be substituted, and a structure formed by bonding through single bonds at most three aromatic rings which may be substituted; $R^1$ represents —COOH, —COOR$^4$, or —COO$^−$M; $R^4$ represents a linear or branched alkyl group having 1 to 5 carbon atoms which may be substituted or an aromatic ring which may be substituted; M represents a monovalent or polyvalent metal cation; n represents a positive number larger than 1; an $R^1$ group in the formula is substituted into the aromatic ring of E; and a hydrogen atom in the aromatic ring, which is not substituted with $R^1$, may be substituted, wherein the polymer compound comprises as a copolymer composition a repeating unit structure having a polycarboxylic acid represented by the general formula (2) on a side chain and a repeating unit structure having a monocarboxylic acid represented by the following general formula (9) on a side chain:

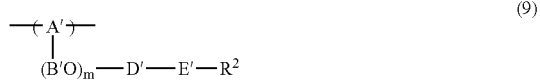

wherein A' represents a polyalkenyl ether group which may be substituted; B' represents a linear or branched alkylene group having 1 to 15 carbon atoms which may be substituted; m represents an integer from 0 to 30; when m is larger than 1, B' may be different from each other; D' represents a single bond or a linear or branched alkylene group having 1 to 10 carbon atoms which may be substituted; E' represents any one of an aromatic ring which may be substituted, a condensed ring which may be substituted, a structure formed by bonding through single bonds at most three aromatic rings which may be substituted, and a methylene group; $R^2$ represents —COOH, —COOR$^3$, or —COO$^-$M; $R^3$ represents a linear or branched alkyl group having 1 to 5 carbon atoms which may be substituted or an aromatic ring which may be substituted; M represents a monovalent or polyvalent metal cation; an $R^2$ group in the formula is substituted for a hydrogen atom in the aromatic ring or the methylene group of E'; and a hydrogen atom in the aromatic ring or the methylene group, which is not substituted with $R^2$, may be substituted.

2. A polymer compound according to claim 1, which is a block polymer having at least two block segments, the polymer compound comprising:

the copolymer composition in at least one block segment of the block polymer.

* * * * *